(12) United States Patent
Moore, II et al.

(10) Patent No.: US 7,169,942 B2
(45) Date of Patent: Jan. 30, 2007

(54) CANNABINOID DERIVATIVES, METHODS OF MAKING, AND USE THEREOF

(75) Inventors: Bob M. Moore, II, Nesbit, MS (US); Antonio M. Ferreira, Memphis, TN (US); Mathangi Krishnamurthy, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/850,588

(22) Filed: May 20, 2004

(65) Prior Publication Data

US 2004/0242593 A1 Dec. 2, 2004

Related U.S. Application Data

(60) Provisional application No. 60/472,316, filed on May 20, 2003.

(51) Int. Cl.
*C07D 311/80* (2006.01)
*C07D 409/04* (2006.01)
*C07D 407/04* (2006.01)

(52) U.S. Cl. .................. 549/390; 549/10; 549/11; 549/14; 549/22; 549/30; 549/39; 549/347

(58) Field of Classification Search ............ 549/390, 549/370, 11, 14, 22, 30, 39, 347, 10
See application file for complete search history.

(56) References Cited

U.S. PATENT DOCUMENTS

| | | | |
|---|---|---|---|
| 3,901,926 A | | 8/1975 | Winn et al. |
| 3,915,996 A | | 10/1975 | Wright et al. |
| 3,941,782 A | | 3/1976 | Harris et al. |
| 5,747,524 A | | 5/1998 | Cullinan et al. |
| 5,939,429 A | | 8/1999 | Kunos et al. |
| 5,948,777 A | | 9/1999 | Bender et al. |
| 6,100,259 A | | 8/2000 | Xiang et al. |
| 6,284,788 B1 | | 9/2001 | Mittendorf et al. |
| 6,344,474 B1 | | 2/2002 | Maruani et al. |
| 6,448,288 B1 | | 9/2002 | Burstein et al. |
| 6,509,367 B1 | | 1/2003 | Martin et al. |
| 6,563,009 B1 | | 5/2003 | Kunos et al. |
| 6,610,737 B1 * | | 8/2003 | Garzon et al. ............. 514/454 |
| 6,642,258 B1 | | 11/2003 | Bourrie et al. |
| 6,653,304 B2 | | 11/2003 | Leftheris et al. |
| 6,939,977 B2 * | | 9/2005 | Makriyannis et al. ....... 549/280 |
| 2001/0034344 A1 | | 10/2001 | Mittendorf et al. |
| 2002/0022653 A1 | | 2/2002 | Burstein et al. |
| 2002/0119972 A1 | | 8/2002 | Leftheris et al. |
| 2002/0173528 A1 | | 11/2002 | Fride et al. |
| 2003/0087933 A1 | | 5/2003 | Blanchard et al. |
| 2003/0096844 A1 | | 5/2003 | Kozlowski et al. |
| 2003/0232859 A1 | | 12/2003 | Kozlowski et al. |
| 2004/0010013 A1 | | 1/2004 | Friary et al. |
| 2004/0039048 A1 | | 2/2004 | Guzman Pastor et al. |
| 2004/0044051 A1 | | 3/2004 | Kozlowski et al. |
| 2004/0077650 A1 | | 4/2004 | Dow |

OTHER PUBLICATIONS

Bailey et al, J. of Chromatography, vol. 87,p.263-266 (1973).*
Papahatjis et al, J. of Heterocyclic Chem., vol. 33, p. 559-562 (1996).*
Keimowitz et al., "QSAR Analysis of $\Delta^8$-THC Analogues: Relationship of Side-Chain Conformation to Cannabinoid Receptor Affinity and Pharmacological Potency," *J. Med. Chem.* 43:59-70 (2000).
Papahatjis et al., "Pharmacophoric Requirements for the Cannabinoid Side Chain Probing the Cannabinoid Receptor Subsite at C1," *J. Med. Chem.* 46:3221-3229 (2003).
Krishnamurthy, Mathangi, "Probing The Ligand-Binding Pocket Of The Cannabinoid Receptors: Design and Synthesis of Novel Ligands," A Dissertation Presented for The Graduate Studies Counsel, The University of Tennessee Health Science Center; pp. 176-178, Dec. 2005.
Krishnamurthy et al., "Synthesis And Testing of Novel Phenyl Substituted Side-Chain Analogues of Classical Cannabinoids," *Bioorganic & Medicinal Chemistry Letters* 13 (2003); 3487-3490.
Nadipuram, et al., "Synthesis And Testing Of Novel Classical Cannabinoids: Exploring The Side Chain Ligand Binding Pocket Of The CB1 and CB2 Receptors," *Bioorganic & Medicinal Chemistry* 11 (2003); 3121-3132.

* cited by examiner

*Primary Examiner*—Bernard Dentz
(74) *Attorney, Agent, or Firm*—O'Melveny & Myers LLP

(57) ABSTRACT

1'-substituted cannabinoid derivatives of delta-8-tetrahydrocannabinol, delta-9-tetrahydrocannabinol, and delta-6a-10a-tetrahydrocannabinol that have affinity for the cannabinoid receptor type-1 (CB-1) and/or cannabinoid receptor type-2 (CB-2). Compounds having activity as either agonists or antagonists of the CB-1 and/or CB-2 receptors can be used for treating CB-1 or CB-2 mediated conditions.

13 Claims, 13 Drawing Sheets

A.
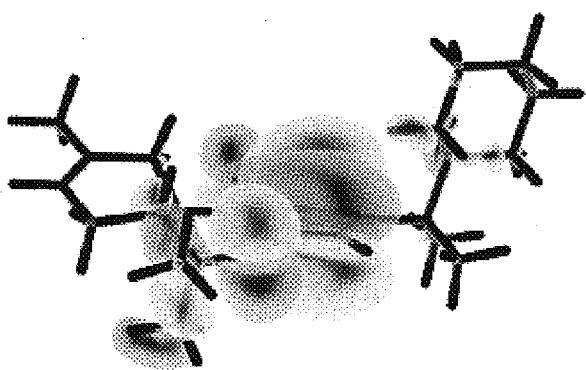
B.
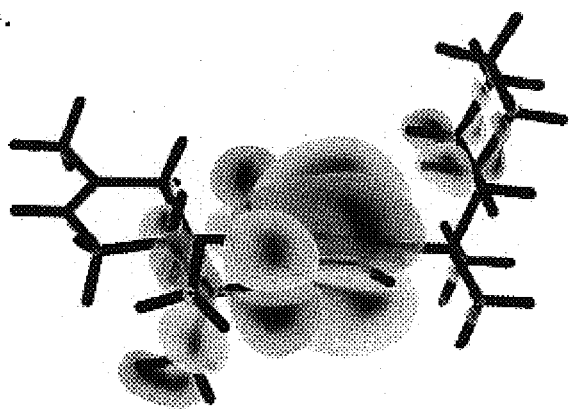
Figures 6A-B a) RMgBr, THF, reflux, 3hrs b) 6N HCl, reflux c) BF₃-Et₂O, ethanedithiol, CH₂Cl₂, rt, overnight
d) Me₂Zn, TiCl₄ e) BBr₃, 0 °C, f) cis-Menth-2-ene-1,8-diol, p-TsOH, benzene, 80 °C

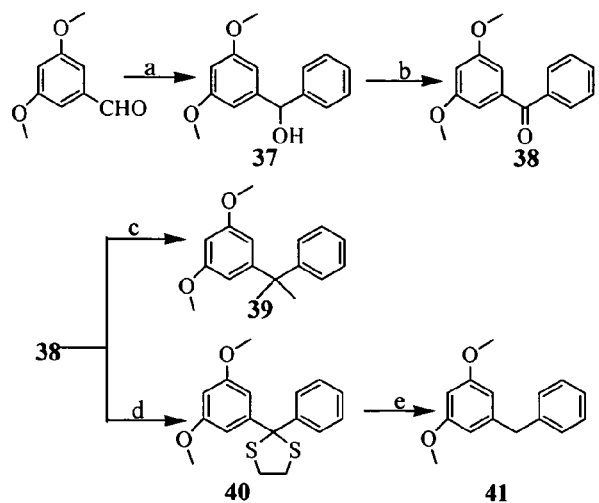

Reagents and conditions: (a) Phenyl magnesium bromide, THF, 10% HCl/ -20°C (b) PCC, CH$_2$Cl$_2$/ room temp (c) Dimethyl zinc, Titanium(IV) chloride, CH$_2$Cl$_2$/-40°C (d) ethane dithiol, BF$_3$-diethyl etherate, CH$_2$Cl$_2$/ room temp (e) Raney Nickel, EtOH/EtOAc, reflux

Figure 8A

Scheme 2.

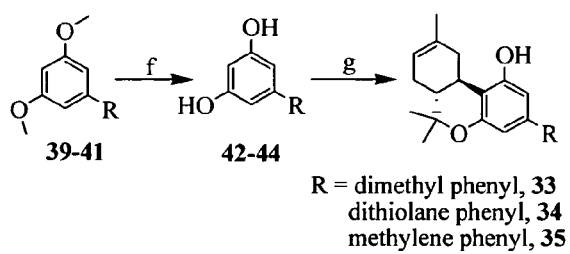

Reagents and conditions: (f) BBr$_3$, CH$_2$Cl$_2$/ 0°C - room temp (g) cis-p-menthene-1,8-diol, p-toluene sulfonic acid, benzene/80°C (h) AgNO$_3$, MeOH/ room temp

Figure 8B

CANNABINOID DERIVATIVES, METHODS OF MAKING, AND USE THEREOF

This application claims the benefit of U.S. Provisional Patent Application Ser. No. 60/472,316 filed May 20, 2003, which is hereby incorporated by reference in its entirety.

FIELD OF THE INVENTION

The present invention relates generally to cannabinoid derivatives of delta-8-tetrahydrocannabinol ($\Delta^8$-THC), delta-9-tetrahydrocannabinol ($\Delta^9$-THC), and delta-6a-10a-tetrahydrocannabinol ($\Delta^{6a-10a}$-THC) that are active as either agonists or antagonists of the cannibinoid receptor type-1 (CB-1) and/or cannabinoid receptor type-2 (CB-2), and their use for treating CB-1 or CB-2 mediated conditions.

BACKGROUND OF THE INVENTION

Delta-9-tetrahydrocannabinol ($\Delta^9$-THC) was isolated and identified as the major active constituent of marijuana in 1964 by Mechoulam and coworkers (Gaoni et al., *J. Am. Chem. Soc.* 86:1646 (1964)). In the following decades, the CB1 and CB2 receptors were discovered, characterized and shown to be responsible for the actions of $\Delta^9$-THC (Gernard et al., *Biochem. J.* 279:129 (1991); Skaper et al., *Proc. Natl. Acad. Sci. USA* 93:3984 (1996); Matsuda et al., *Nature* 346:61 (1990); Munro et al., *Nature* 365:61 (1993)). The CB1 and CB2 receptors have since gained attention as potential therapeutic targets for the development of antiobesity (Di Marzo et al., *Nature* 410:822 (2001)), anticancer (Palolaro et al., *Prostaglandins Leukot. Essent. Fatty Acids* 66:319 (2002)), analgesic (Palmer et al., *Chem. Phys. Lipids* 121:3 (2002)), and antiglaucoma agents (Porcella et al., *Eur. J. Neurosci.* 13:409 (2001); Chien et al., *Arch. Ophthalmol.* 121:87 (2003)). Efforts to develop therapeutic agents have resulted in the identification of a number of structurally distinct classes of compounds that bind to the cannabinoid receptors, these include the classical cannabinoids ($\Delta^9$-THC), the non-classical cannabinoids such as CP55,940 (Melvin et al., *Med. Chem.* 27:67 (1984)), the diarylpyrazoles such as AM-251 (Lan et al., *J. Med. Chem.* 42:769 (1999)), and aminoalkylindoles such as WIN-55212 (D'Ambra et al., *J. Med. Chem.* 35:124 (1992)). By far the most extensively studied cannabinoid analogs in terms of the pharmacology and SAR are the classical and non-classical cannabinoids.

The binding affinity of the classical cannabinoids (CCBs) and non-classical cannabinoids to the CB1 receptor can generally be defined in terms of a three point and four point pharmacophore model, respectively (Seltzman, *Curr. Med. Chem.* 6:685 (1999)). The structural elements that form the three point pharmacophore of the CCB analogs are: (1) a phenolic group in the C1 position of the aromatic ring (Razdan, *Pharmac. Rev.* 38:75 (1986); Uliss et al., *J. Med. Chem.* 18:213 (1975)); (2) an unsaturated $\Delta^8$ or $\Delta^9$ C ring with an exocyclic C11 methyl or hydroxy methyl, or alternatively a saturated C ring containing a 9-β-hydroxyl, 9-β-hydroxy methyl, or 9-keto functional group (Thomas et al., *Mol. Pharmacol.* 40:656 (1991); Wilson et al., *J. Med. Chem.* 19:1165 (1976); Melvin et al., *Mol. Pharmacol.* 44:1008 (1993); Mechoulam et al., *Experientia* 44:762 (1988); and (3) a C3 aliphatic side chain ranging from 3 to 7 carbons wherein heptyl analogs represent the optimum side chain length. In addition to the basic pharmacophore model, substitution of the C3 side chain with 1',1'-dimethyl, 1',2'-dimethyl, and 1',1'-dithiolane generally enhances the activity of the CCBs (Huffman et al., *Tetrahedron* 53:1557 (1997); Huffman et al., *Bioorganic Med. Chem. Lett.* 7:2799 (1997); Guo et al., *J. Med. Chem.* 37:3867 (1994); Devane et al., *J. Med Chem.* 35:2065 (1992); Tius et al., *Life Sci.* 56:2007 (2007); Huffman et al., *J. Med Chem.* 39:3875 (1996)).

The understanding of the interplay between the pharmacophoric elements of CCBs and the ligand binding pocket (LBP) have been significantly refined as a result of QSAR studies and site directed mutagenesis of the LBP. Computational studies have identified the requirement for a hydrogen bond donor/acceptor pair in the C1 region of CCBs (Thomas et al., *Mol. Pharmacol.* 40:656 (1991); Schmetzer et al., *J. Computer-Aided Mol. Design* 11:278 (1997); Reggio et al., *J. Med. Chem.* 32:1630 (1989); Johnson et al., *Cannabinoids as Therapeutic Agents*, Boca Raton, Fla., CRC Press (1986)), a result proposed to correlate with an interaction of the C1 hydroxyl with a critical Lys192 in the CB1 receptor (Song et al., *Mold. Pharmacol.* 49:891 (1996); Chin et al., *J. Neurochem.* 70:280 (1998)). An additional donor/acceptor pair between Tyr275 and the CCBs containing a hydroxyl in the C9 region may be responsible for the increased CB1 affinity relative to $\Delta^9$-THC (McAllister et al., *Biochem. Pharmacol.* 63:2121 (2002), which is hereby incorporated by reference in its entirety).

The intramolecular geometries of the C1 and C9 substituents are tightly defined by the rigid ring system of the CCBs, however QSAR studies indicate moderate to high conformational flexibility in the C3 side chains (Schmetzer et al., *J. Computer-Aided Mol. Design* 11:278 (1997); Papahatjis et al., *J. Med. Chem.* 41:1195 (1998); Ryan et al., *Life Sci.* 56:2013 (1995); Keimowitz et al., *J. Med. Chem.* 43:59 (2000). These studies clearly demonstrate the LBP of CB1 prefers a hydrophobic substituent at C3 but the requirement for conformational flexibility remains to be fully elucidated. Progress to this end has been reported in studies of a series of conformationally restricted $\Delta^8$-THC side chain analogs incorporating methylene and methyne functionalities (Keimowitz et al., *J. Med. Chem.* 43:59 (2000)) and 1'-cyclopropyl analogs (Papahatjis et al., *Bioorg. Med. Chem. Lett.* 12:3583 (2002)). The study suggests that the side chain adopts an orthogonal geometry relative to the plane of the aromatic ring with the tail of the side chain folding into a hydrophobic pocket. Despite the incorporation of unsaturation into the side chains, considerable flexibility remains in this set of molecules. The inherent computational limitations in predicting the conformation of a flexible side chain, in the absence of x-ray crystallographic or high resolution NMR data, somewhat limits the ability to predict the preferred side chain geometry and LBP steric requirements of the CB receptors.

There still remains a need for identifying compounds that can be used for therapeutic purposes to affect treatment of conditions or disorders that are mediated by the CB-1 receptor and/or the CB-2 receptor.

The present invention is directed to developing $\Delta^8$-THC, $\Delta^9$-THC, and $\Delta^{6a-10a}$-THC analogs that exhibit activity, either as an agonist or an antagonist, on the CB-1 receptor and/or the CB-2 receptor and can be used to treat conditions or disorders that are mediated by these receptors.

SUMMARY OF THE INVENTION

A first aspect of the present invention relates to cannabinoid analogs according to formula (I) below

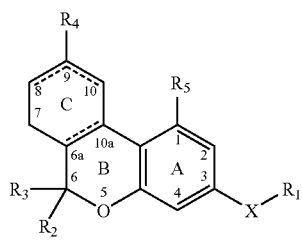

(I)

wherein the C ring contains a double bond at either the $\Delta^8$ position, the $\Delta^9$ position, or the $\Delta^{6a-10a}$ position;

X is selected from the group of C(CH$_3$)$_2$, C(—Y(CH$_2$)$_n$Y—), CH$_2$, C(O),

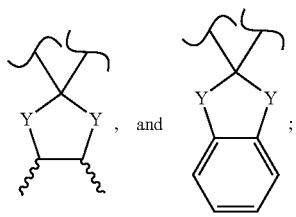

Y is selected from the group of S and O;

R$_1$ is selected from the group of a C3 to C8 cycloalkyl, thiophenyl, furanyl, pyrrolyl, pyridinyl, pyrimidinyl, pyrrolidinyl, biphenyl, 2-napthyl, thiazolyl, benzthiazolyl, methyltetrazolyl,

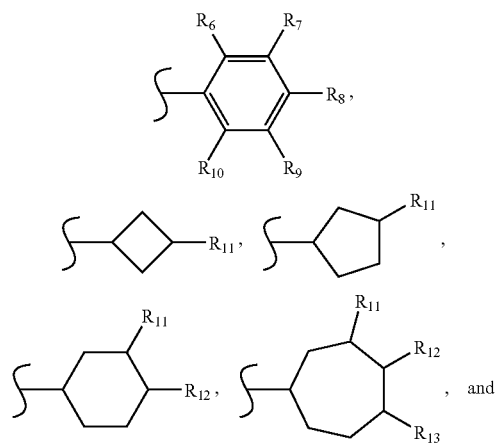

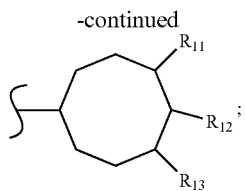

R$_2$ and R$_3$ are methyl for compounds containing a $\Delta^8$ or a $\Delta^9$ double bond, or are independently selected from the group of a C1 to C3 alkyl group and a C1 to C3 alkanol for compounds containing a $\Delta^{6a-10a}$ double bond;

R$_4$ is selected from the group of methyl, methanol, —(CH$_2$)$_m$COOH, and —(CH$_2$)$_m$COH for compounds containing a $\Delta^8$ or a $\Delta^9$ double bond, or is methyl for compounds containing a $\Delta^{6a-10a}$ double bond;

R$_5$ is selected from the group of H, OH, methoxy, and ethoxy;

R$_6$–R$_{10}$ are independently selected from the group of H, OH, C1 to C6 alkyl, halo, amino, C1 to C2 alkylamino, C1 to C2 dialkylamino, amido, C1 to C2 alkylamido, cyano, nitro, C1 to C6 alkoxy, C1 to C6 alcohol, carboxyl containing a C1 to C6 alkyl, carbonyl containing a C1 to C6 alkyl, ester containing a C1 to C6 alkyl group, sulfoxide containing a C1 to C6 alkyl, and sulfone containing a C1 to C6 alkyl;

at least one of R$_{11}$–R$_{13}$ is selected from the group of C1 to C6 alkyl, C1 to C6 alkoxy, fluoro, and chloro, and the other of R$_{11}$–R$_{13}$ can optionally be H;

n is an integer from 2 to 4; and m is an integer that is either 0 or 1.

A second aspect of the present invention relates to a composition that includes a compound according to formula (I) above and a pharmaceutically acceptable carrier.

A third aspect of the present invention relates to a method of modifying the activity of a cannabinoid receptor that includes: providing a compound according to formula (I); and contacting a cannabinoid receptor of a cell with the compound, whereby said contacting modifies the activity of the cannabinoid receptor in the cell.

A fourth aspect of the present invention relates to a method of treating a cannabinoid receptor-mediated condition that includes: providing a compound formula (I), wherein the compound acts as an agonist on the cannabinoid receptor; and administering to a patient an amount of the compound that is effective to treat a cannabinoid receptor-mediated condition.

A fifth aspect of the present invention relates to a method of treating a cannabinoid receptor-mediated condition that includes: providing a compound according to claim 1, wherein the compound acts as an antagonist on the cannabinoid receptor; and administering to a patient an amount of the compound that is effective to treat a cannabinoid receptor-mediated condition.

A sixth aspect of the present invention relates to methods of preparing compounds according to formula (I).

According to one approach, a $\Delta^8$-THC or $\Delta^9$-THC compound of the present invention is prepared by reacting an intermediate compound having the structure of formula (II)

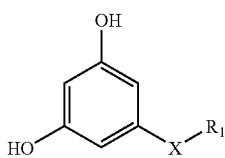

(II)

with a reactant according to either formula (IIIa) or formula (IIIb)

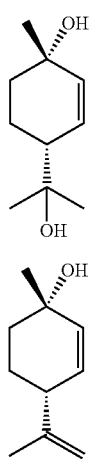

(IIIa)

(IIIb)

under conditions effective to form a compound according to claim 1 that contains a double bond at the $\Delta^8$ or $\Delta^9$ position of the C ring.

According to another approach, $\Delta^{6a-10a}$-THC analogs can be prepared by reacting an intermediate compound having the structure of formula (IV)

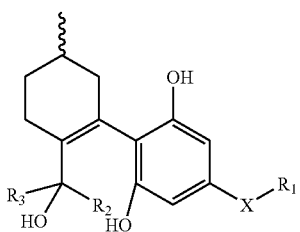

(IV)

with an acid (such as trifluoroacetic acid or hydrobromic acid) under conditions effective to form a compound of the present invention that contains a double bond at the $\Delta^{6a-10a}$ position of the C ring.

Several compounds of the present invention have a demonstrated affinity for either the CB-1 receptor, CB-2 receptor, or both, and several compounds show selectivity of one receptor over the other. The compounds of the present invention offer a major benefit in that a wide diversity of 1'-aromatic THC with one or more functional groups can be prepared in accordance with the present invention. Such compounds were not traditionally available, particularly with the previously known 1'-linear hydrocarbon THC analogs. Moreover, several compounds have shown improved affinity for the CB-1 and/or CB-2 receptor, as well as efficacy for treating a condition that is mediated by a CB receptor, as evidence by in vitro or in vivo testing.

BRIEF DESCRIPTION OF THE DRAWINGS

FIGS. 6A–B illustrate orbital diagrams of the calculated HOMO at the B3LYP/6-31G(p,d) level of theory. The shape of the orbital lobes centered on the cyclohexyl hydrogen atoms is suggestive of antibonding σ orbitals associated with hydrogen 1s atomic orbitals. FIG. 6A demonstrates a repulsive interaction between two of the cyclohexyl hydrogen atoms and the aromatic orbital lobes on ring A whereas FIG. 6B shows only one such interaction. There is noticeable distortion of the orbital lobes associated with ring A, which supports a significant repulsion between the cyclohexyl hydrogen atoms and the electron density associated with the aromatic ring.

FIGS. 8A–B illustrate synthesis schemes used to prepare various $\Delta^8$-THC analogs of the present invention having a 1'-phenyl substituent.

DETAILED DESCRIPTION OF THE INVENTION

Figure 1:
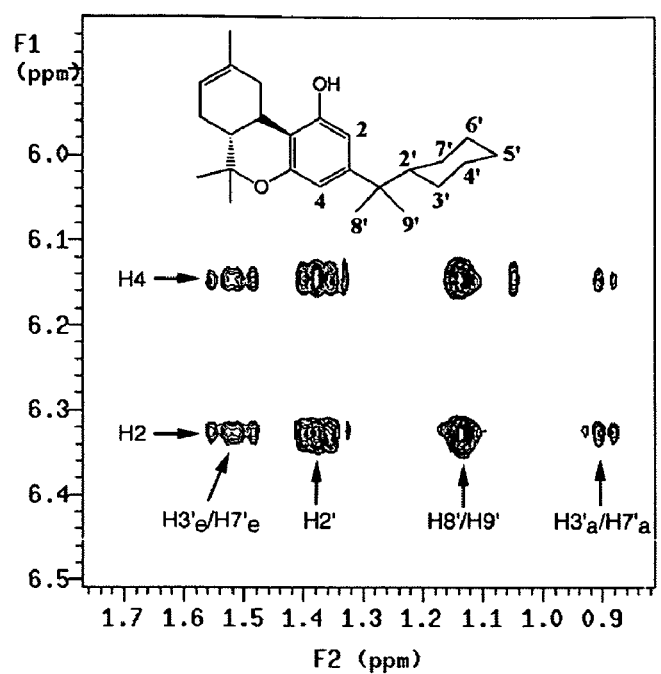
FIG. 1 is a partial 2D NOESY spectra (300 ms mixing time) of compound 28 showing the NOEs between the aromatic protons H2/H4 and the methylene, H3'/H7', and methyne proton, H2', on the cyclohexyl ring.

The present invention relates to cannabinoid analogs according to formula (I) below

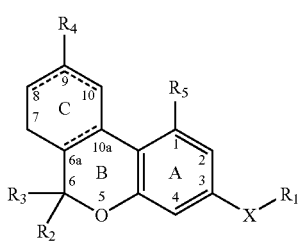

(I)

wherein
X is selected from the group of $C(CH_3)_2$, $C(-Y(CH_2)_n Y-)$, $CH_2$, $C(O)$,

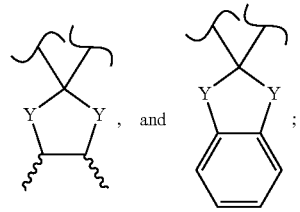
, and ;

Y is selected from the group of S and O;
R$_1$ is selected from the group of a C3 to C8 cycloalkyl, thiophenyl, furanyl, pyrrolyl, pyridinyl, pyrimidinyl, pyrrolidinyl, biphenyl, 2-napthyl, thiazolyl,

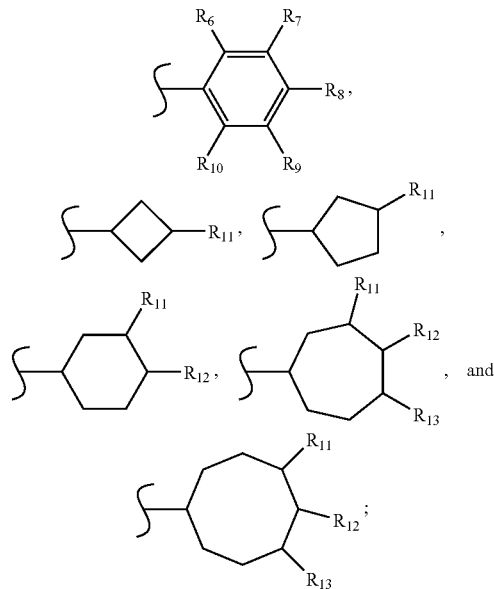
, and

;

R$_2$ and R$_3$ are methyl for compounds containing a $\Delta^8$ or a $\Delta^9$ double bond, or are independently selected from the group of a C1 to C3 alkyl group and a C1 to C3 alkanol for compounds containing a $\Delta^{6a-10a}$ double bond;

R$_4$ is selected from the group of methyl, methanol, $-(CH_2)_m COOH$, and $-(CH_2)_m COH$ for compounds containing a $\Delta^8$ or a $\Delta^9$ double bond, or is methyl for compounds containing a $\Delta^{6a-10a}$ double bond;

R$_5$ is selected from the group of H, OH, methoxy, and ethoxy;

R$_6$–R$_{10}$ are independently selected from the group of H, OH, C1 to C6 alkyl, halo, amino, C1 to C2 alkylamino, C1 to C2 dialkylamino, amido, C1 to C2 alkylamido, cyano, nitro, C1 to C6 alkoxy, C1 to C6 alcohol, carboxyl containing a C1 to C6 alkyl, carbonyl containing a C1 to C6 alkyl, ester containing a C1 to C6 alkyl group, sulfoxide containing a C1 to C6 alkyl, and sulfone containing a C1 to C6 alkyl;

at least one of R$_{11}$–R$_{13}$ is selected from the group of C1 to C6 alkyl, C1 to C6 alkoxy, fluoro, and chloro, and the other of R$_{11}$–R$_{13}$ can optionally be H;

n is an integer from 2 to 4; and m is an integer that is either 0 or 1.

The compounds according to formula (I) can contain either a $\Delta^8$ double bond, a $\Delta^9$ double bond, or a $\Delta^{6a-10a}$ double bond within the C ring. The stereochemistry of the compounds of formula (I) is not shown above, although the $\Delta^8$- and $\Delta^9$-THC analogs have a specific stereochemistry at the 6a and 10a positions between the B,C rings. Stereochemistry of preferred $\Delta^8$- and $\Delta^9$-THC analogs is shown below.

As used herein, alkyl groups or alkyl substituents of a larger group (e.g., of alkoxy, alkylamino, dialkylamino, alkylamido, alcohol, carboxyl, carbonyl, ester, sulfoxide, and sulfone groups) can be straight- or branched-chain alkyls, including without limitation methyl, ethyl, propyl, butyl, pentyl, hexyl, 1-methylethyl, 1-methylpropyl, t-butyl, 1-methylpentyl, 2-methylpentyl, 3-methylpentyl, 1-ethylbutyl, 2-ethylbutyl, etc. Straight-chain alkyl groups are preferred. C1 to C3 alkyl groups contain a total of three carbon atoms, C1 to C6 alkyl groups contain a total of six carbon atoms, etc.

Preferred alkyl groups are methyl, ethyl, and propyl. Preferred alkoxy groups are methoxy and ethoxy. Preferred carboxyl groups are methylcarboxyl, ethylcarboxyl, and propylcarboxyl. Preferred aldehyde groups can be carbaldehyde or acetaldehyde groups. Preferred carbonyl groups are methanone, ethanone, and propanone groups. Preferred ester groups can have their carbonyl group bound directly to the phenyl ring or displaced therefrom (with intervening alkyl substituents) containing either methyl, ethyl, or propyl terminal groups. Preferred sulfoxides can have the sulfur bonded directly to the phenyl ring or displaced therefrom (with intervening alkyl substituents) containing either methyl, ethyl, or propyl terminal groups. Preferred sulfones can have the sulfur bonded directly to the phenyl ring or displaced therefrom (with intervening alkyl substituents) containing either methyl, ethyl, or propyl terminal groups.

Preferred $R_1$ groups are cyclopentyl, cyclohexyl, cycloheptyl, 2-thiophenyl, 3-thiophenyl, 2-furanyl, 3-furanyl, 2-pyrrolyl, 2-pyridinyl, 3-pyridinyl, 4-pyridinyl, 2-pyrrolidinyl, 3-pyrrolidinyl, 4-pyrrolidinyl, biphenyl, 2-napthyl, 5-pyrimidinyl, 2-thiazolyl, 2-benzthiazolyl, methyltetrazolyl, phenyl, o-methylphenyl, m-methylphenyl, p-methylphenyl, m,p-dimethylphenyl, o,p-dimethylphenyl, m-ethylphenyl, p-ethylphenyl, m,p-diethylphenyl, m-methanolphenyl, m-ethanol-phenyl, p-methanol-phenyl, p-ethanolphenyl, p-chlorophenyl, p-fluorophenyl, p-bromophenyl, m-aminophenyl, p-aminophenyl, m-methylaminophenyl, p-methylaminophenyl, N,N-dimethyl-m-aminophenyl, N,N-dimethyl-p-aminophenyl, m-amidophenyl, p-amidophenyl, m-methylamidophenyl, p-methylamidophenyl, m-cyanophenyl, p-cyanophenyl, m-nitrophenyl, p-nitrophenyl, o-methoxyphenyl, m-methoxyphenyl, p-methoxyphenyl, m-ethoxyphenyl, p-ethoxyphenyl, m-methylsulfoxide-phenyl, m-ethylsulfoxide-phenyl, p-methylsulfoxide-phenyl, p-ethylsulfoxide-phenyl, m-methylsulfone-phenyl, m-ethylsulfone-phenyl, p-methylsulfone-phenyl, p-ethylsulfone-phenyl, m-methylketone-phenyl, p-methylketone, m-ethylketone-phenyl, p-ethylketone-phenyl, m-methanoate-phenyl, p-methanoate-phenyl, m-ethanoate-phenyl, p-ethanoate-phenyl, 2-methylcyclopentyl, 2-methoxycyclopentyl, 2-ethylcyclopentyl, 2-ethoxycyclopentyl, 2-chlorocyclopentyl, 2-fluorocyclopentyl, 2-methylcyclohexyl, 2-methoxycyclohexyl, 2-ethylcyclohexyl, 2-ethoxycyclohexyl, 2-chlorocyclohexyl, 2-fluorocyclohexyl, 3-methylcyclohexyl, 3-methoxycyclohexyl, 3-ethylcyclohexyl, 3-ethoxycyclohexyl, 3-chlorocyclohexyl, 3-fluorocyclohexyl, 3-methylcycloheptyl, 3-methoxycycloheptyl, 3-ethylcycloheptyl, 3-ethoxycycloheptyl, 3-chlorocycloheptyl, 3-fluorocycloheptyl, 4-methylcycloheptyl, 4-methoxycycloheptyl, 4-ethylcycloheptyl, 4-ethoxycycloheptyl, 4-chlorocycloheptyl, 4-fluorocycloheptyl, 4-methylcyclooctyl, 4-methoxycyclooctyl, 4-ethylcyclooctyl, 4-ethoxycyclooctyl, 4-chlorocyclooctyl, 4-fluorocyclooctyl, 5-methylcyclooctyl, 5-methoxycyclooctyl, 5-ethylcyclooctyl, 5-ethoxycyclooctyl, 5-chlorocyclooctyl, and 5-fluorocyclooctyl. Of these compounds, thiophenyl, substituted cyclohexyl, and substituted cyclophenyl groups are most preferred.

Preferred $R_2$ and $R_3$ groups (i.e., when the C ring contains a $\Delta^{6a-10a}$ double bond) include methyl, ethyl, methanol, and ethanol. $R_2$ and $R_3$ can be the same or different. Of these, methyl, methanol, and ethanol are most preferred.

Preferred $R_4$ groups include methyl, methanol, carboxylic acid, and carbaldehyde. Of these, methanol and methyl are most preferred.

Because $R_5$ influence the selectivity of the compounds of the present invention, different groups are preferred for CB-1 selective compounds (e.g., OH group) and for CB-2 selective compounds (e.g., hydrogen, methoxy, and ethoxy).

Preferred X groups are $CH_2$, $C(O)$, $C(CH_3)_2$, $C(-S(CH_2)_2S-)$, $C(-S(CH_2)_3S-)$, $C(-O(CH_2)_2O-)$, and $C(-O(CH_2)_3O-)$. Of these, the gem-dimethyl group and keto group are presently most preferred.

Particularly preferred compounds include, without limitation, the compounds listed below.

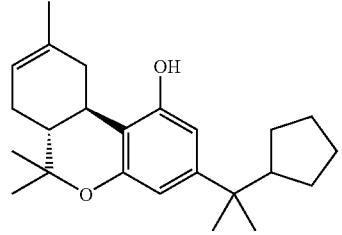

gem-dimethyl-cyclopentyl-$\Delta^8$-THC

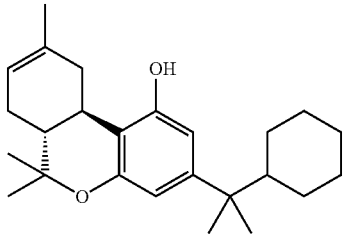

gem-dimethyl-cyclohexyl-$\Delta^8$-THC

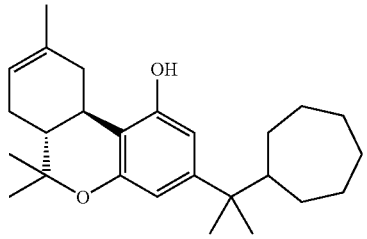

gem-dimethyl-cycloheptyl-$\Delta^8$-THC

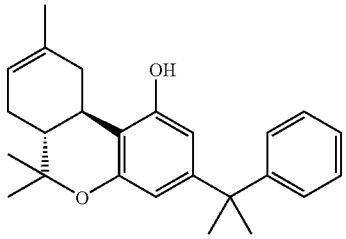

gem-dimethyl-phenyl-$\Delta^8$-THC

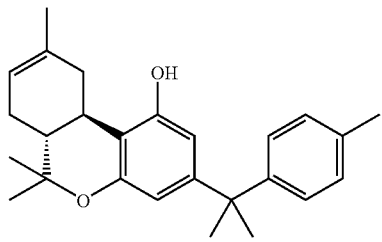

gem-dimethyl-p-methylphenyl-Δ⁸-THC

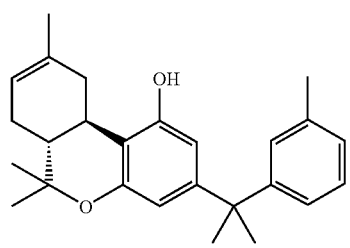

gem-dimethyl-m-methylphenyl-Δ⁸-THC

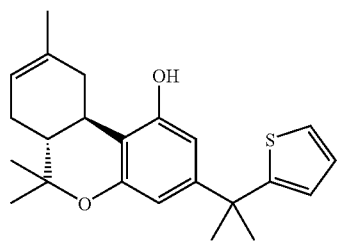

gem-dimethyl-2-thiophenyl-Δ⁸-THC

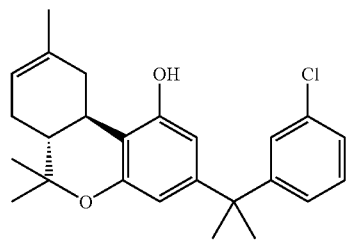

gem-dimethyl-m-chlorophenyl-Δ⁸-THC

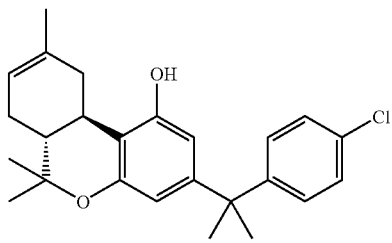

gem-dimethyl-p-chlorophenyl-Δ⁸-THC

The present invention further relates to methods of making the compounds of formula (I).

The Δ⁸-THC analogs can generally be prepared according to the synthesis protocol defined in Scheme 1 below.

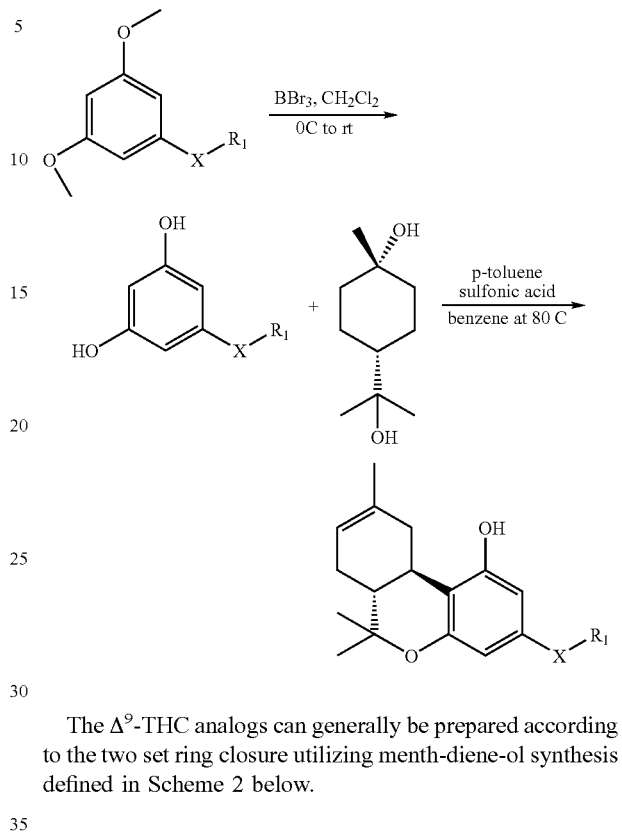

The Δ⁹-THC analogs can generally be prepared according to the two set ring closure utilizing menth-diene-ol synthesis defined in Scheme 2 below.

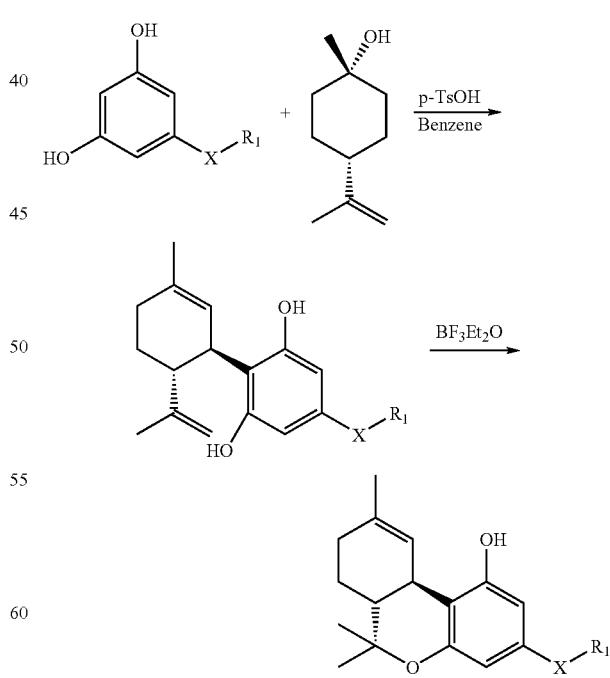

The Δ$^{6a\text{-}10a}$-THC analogs can generally be prepared, either as a racemic mixture or as an optically pure isomer, using the beta ketoester as illustrated in Scheme 3 below.

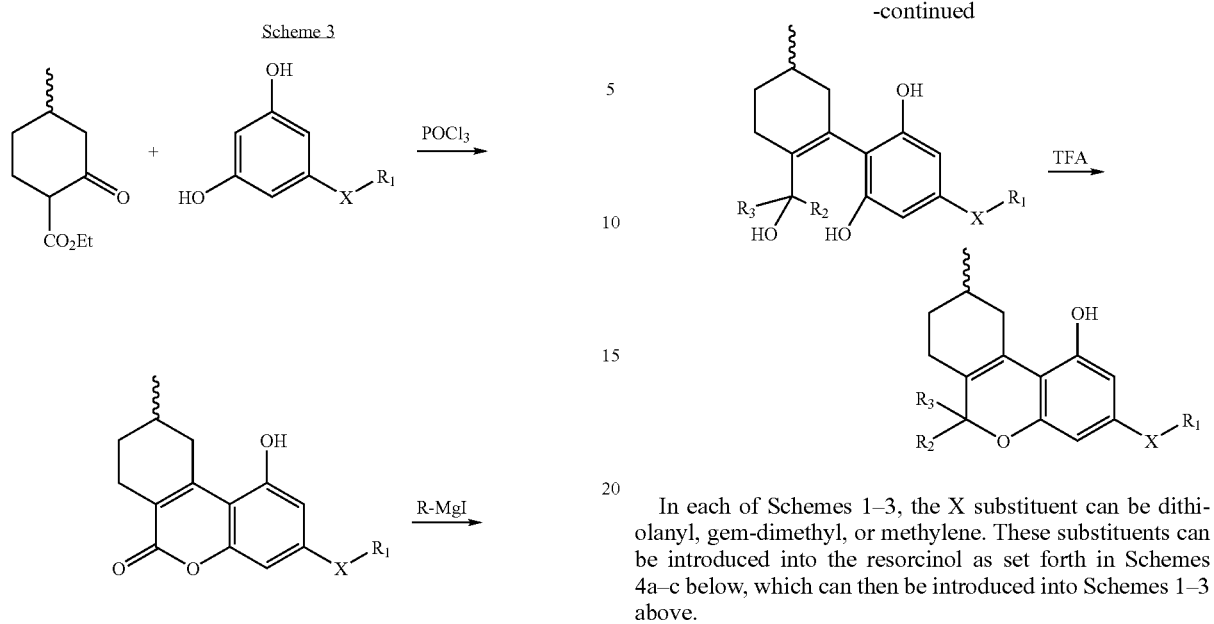
In each of Schemes 1–3, the X substituent can be dithiolanyl, gem-dimethyl, or methylene. These substituents can be introduced into the resorcinol as set forth in Schemes 4a–c below, which can then be introduced into Schemes 1–3 above.
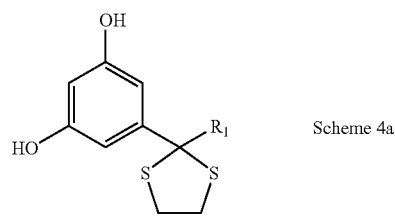
Scheme 4a
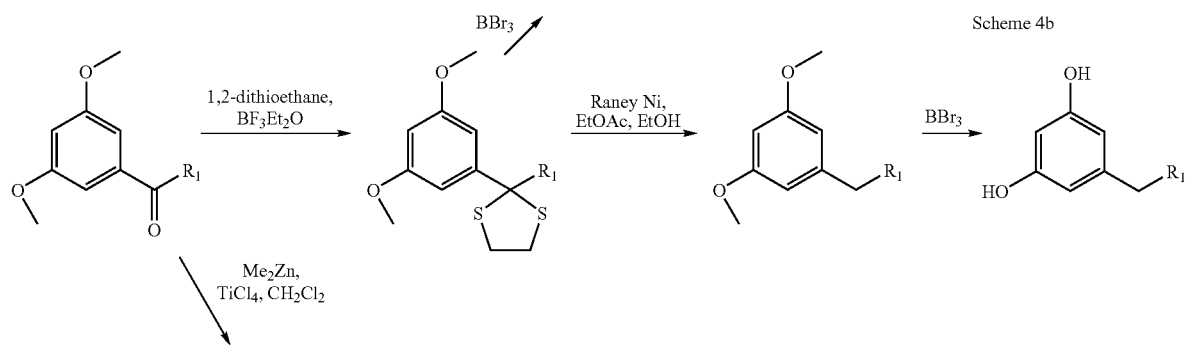
Scheme 4b
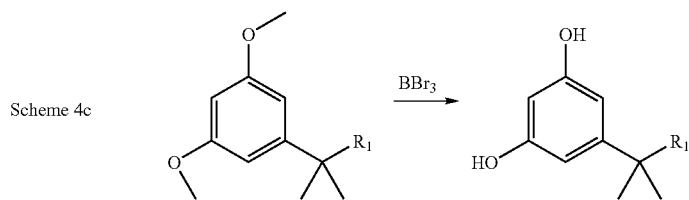
Scheme 4c By way of example, compounds of the present invention containing a keto substituent as X can be formed from a compound containing a dithiolanyl as X. This reaction scheme is set forth below as Schemes 4d.

Scheme 4d

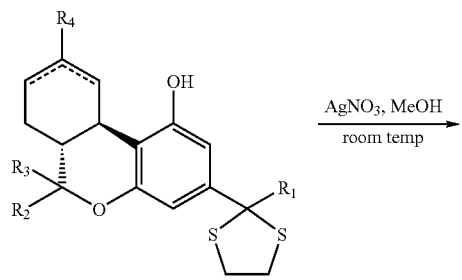

AgNO₃, MeOH
room temp
→

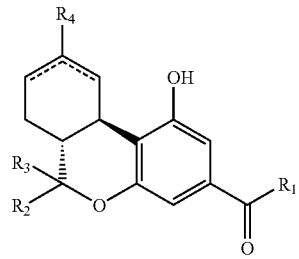

-continued

Although the compounds shown above represent $\Delta^8$- or $\Delta^9$-THC analogs of the present invention, the same procedure can be employed for $\Delta^{6a-10a}$-THC analogs of the present invention.

By way of example, compounds of the present invention containing alternative substituents as X can be formed from the compound containing a keto substituent as X (e.g., formed in Scheme 4d). These reaction schemes are set forth below as Schemes 4e–4g.

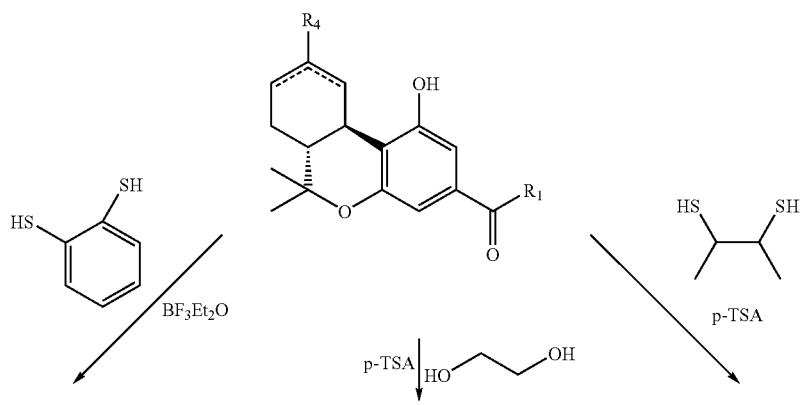

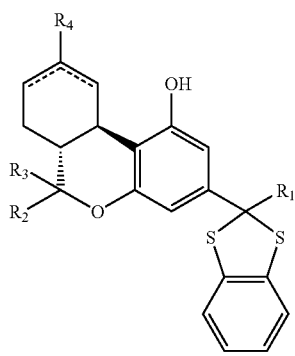

Scheme 4e

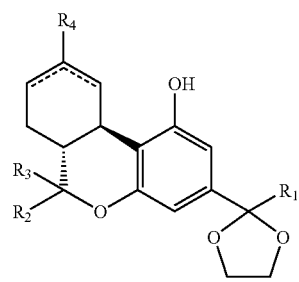

Scheme 4f

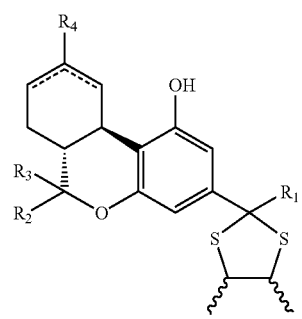

Scheme 4g

Although the compounds shown above represent $\Delta^8$- or $\Delta^9$-THC analogs of the present invention, the same procedure can be employed for $\Delta^{6a-10a}$-THC analogs of the present invention.

By way of example, compounds of the present invention containing other than a hydroxyl group at the $R_5$ position can be prepared according to the schemes set forth in Schemes 5a and 5b below.

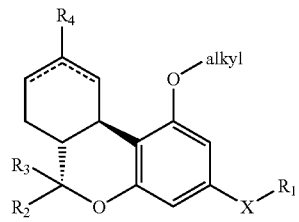

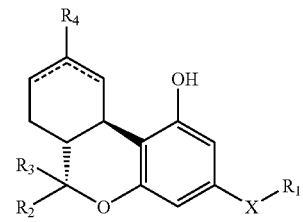

Scheme 5a

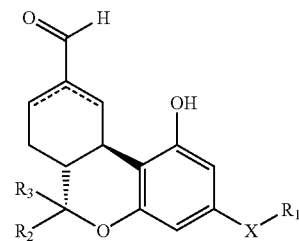

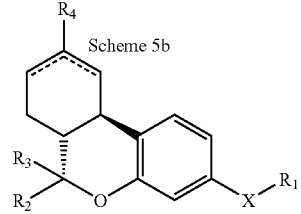

Scheme 5b

Although the compounds shown above in Schemes 5a,5b represent $\Delta^8$- or $\Delta^9$-THC analogs of the present invention, the same procedure can be employed for $\Delta^{6a-10a}$-THC analogs of the present invention.

By way of example, $\Delta^8$- or $\Delta^9$-THC analogs of the present invention that contain a carboxyl or aldehyde group at the $R_4$ position can be prepared according to the schemes set forth in Schemes 6a and 6b below, respectively.

Scheme 6a

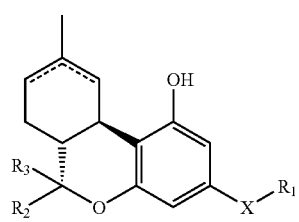

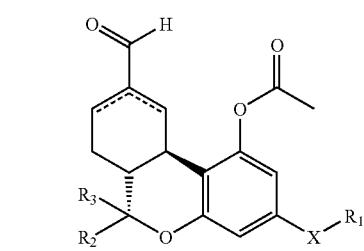

-continued
Scheme 6b

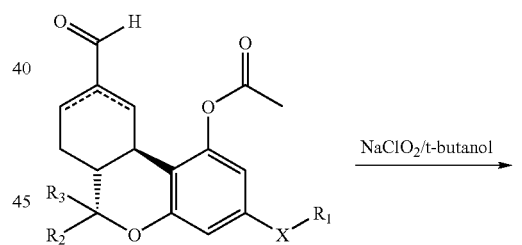

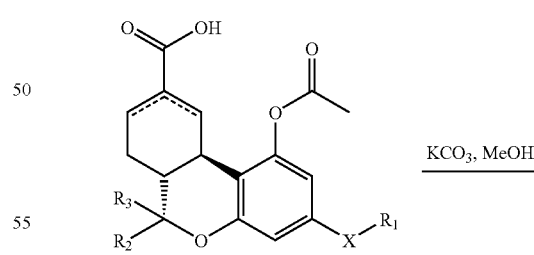

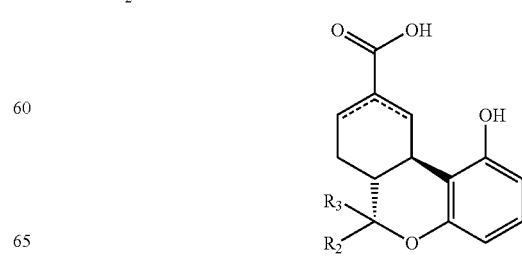

Either the carboxyl group or the aldehyde group can be reduced under standard conditions (e.g., NaBH$_4$ or LiAlH$_4$) to form a methanol group.

In each of Schemes 1–3, the R$_1$ substituent can be a hetero-ring, preferably a hetero-aromatic ring. These hetero-ring R$_1$ substituents can be introduced via Grignard reaction, allowing for preparation of the resorcinol derivative shown in Scheme 7 below. The resorcinol can then be introduced into Schemes 1–3 above for preparation of the compounds of the present invention.

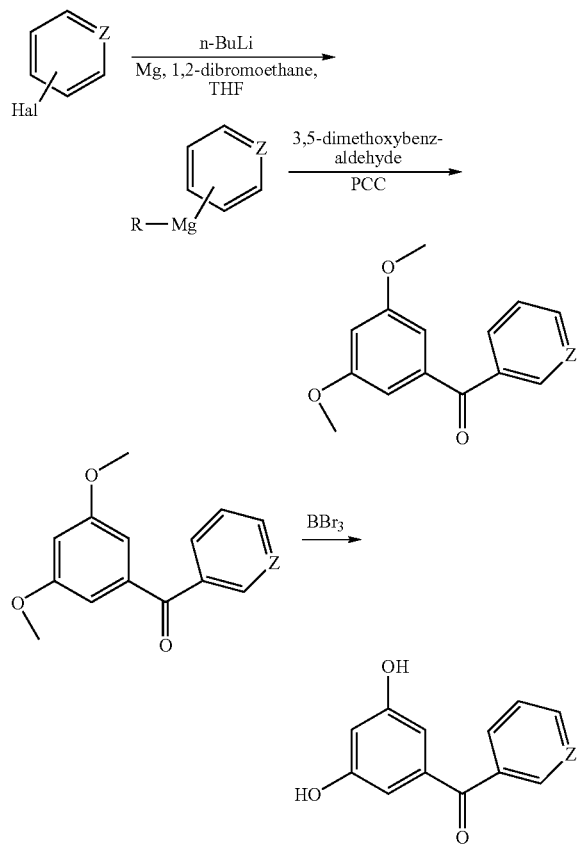

Scheme 7

In Scheme 7, the hetero-ring is shown to be unsubstituted. However, it should be appreciated that ring substituents can be introduced into the ring prior to formation of the resorcinol. The six-member ring containing a single hetero atom as illustrated in Scheme 7 is intended to represent any of the above-identified R$_1$ hetero-atom rings.

Further aspects of the present invention concern the use of the compounds of formula (I) for modifying the activity of a cannabinoid receptor and for treating a cannabinoid receptor-mediated condition, disease, or disorder.

In that regard, the present invention also relates to compositions that contain one or more compounds according to formula (I) and a pharmaceutically acceptable carrier.

The one or more compounds are present in an amount effective to achieve the intended purpose of administration. While individual needs vary, determination of optimal ranges of effective amounts of each component is within the skill of the art. The quantity of the one or more compounds administered will vary depending on the patient and the mode of administration and can be any effective amount.

Typical dosages include about 0.01 to about 100 mg/kg·body wt, more preferably between about 0.01 to about 1.0 mg/kg-body wt up to three times a day. Treatment regimen for the administration of the compounds of the present invention can also be determined readily by those with ordinary skill in art. The quantity of the compound administered may vary over a wide range to provide in a unit dosage an effective amount of from about 0.01 to 20 mg/kg of body weight of the patient per day to achieve the desired effect. Single doses are preferably between about 1 mg and about 1000 mg/per dose.

The pharmaceutically acceptable carrier can be any suitable adjuvant, carrier, excipient, stabilizer, or combination thereof, and the pharmaceutical composition can be in solid or liquid form such as, tablets, capsules, powders, solutions, suspensions, or emulsions. Typically, the composition will contain from about 0.01 to 99 percent, preferably from about 20 to 75 percent of active compound(s), together with the adjuvants, carriers and/or excipients.

For oral therapeutic administration, the active compounds can be incorporated with excipients and used in the form of tablets, capsules, elixirs, suspensions, syrups, and the like.

The solid unit dosage forms (e.g., tablet or capsule) can be of the conventional type. For example, the compounds can be combined with one or more lubricants and/or inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

Oral liquid dosages can contain aqueous or alcohol-based carriers, along with sweeteners, such as corn syrup, saccharine, aspartame, etc., natural or artificial flavoring agents, and optionally one or more dyes.

Forms suitable for injectable use include colloidal dispersions, microemulsions, and sterile powders for the extemporaneous preparation of sterile injectable dispersions or microemulsions. In all cases, the form should be sterile and should be fluid to the extent that easy syringability exists. It should be stable under the conditions of manufacture and storage and should be preserved against the contaminating action of microorganisms, such as bacteria and fungi. The solutions or suspensions of the active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol can be utilized in combination with the microemulsions, as preformulations. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds or compositions of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

One preferred composition of the present invention is a microemulsion preparation containing the ingredients listed below:

| Ingredient | mg/dose | Percent w/w |
|---|---|---|
| Poly Ethylene Glycol 300 | 600 | 59.6 |
| Ethanol | 320 | 31.7 |
| Polysorbate 80 | 80 | 7.9 |
| Tocopherol acetate | 7 | 0.7 |
| Disodium EDTA solution | 1 | 0.1 |

Compounds of the present invention can be introduced into the microemulsion preparation at various concentrations/dosages, such as those defined above. In testing, a dosage of 1 mg/dose (0.1 w/w percent) has been used.

Another preferred composition of the present invention is a formulation having the following components: hydrogenated soy phosphatidyl choline (HSPC, 50 mol %), cholesterol (45 mol %), and distearyl phosphotidyl ethanolamine-PEG2000 conjugate (DSPE-PEG2000, 5 mol %). Compounds of the present invention can be introduced into the liposomal preparation at various concentrations/dosages, such as those defined above.

Because the compounds of the present invention bind to the CB-1 and/or CB-2 receptors and act as either agonists or antagonists of those receptors, the compounds of the present invention can be used to modify the activity of one or both of these receptors. This method of the present invention is carried out by contacting a cannabinoid receptor of a cell with a compound of the present invention, whereby the contacting modifies the activity of the cannabinoid receptor in the cell.

The cell having the cannabinoid receptor can either be located ex vivo (i.e., for performing an assay to define the activity of the compound as an agonist or antagonist) or in vivo (i.e., for treating or preventing a cannabinoid receptor mediated condition). CB-1 receptors have been demonstrated to be expressed in the central nervous system, heart, vascular endothelium, uterus, testis, vas deferens, small intestine, or urinary bladder. CB-2 receptors have been demonstrated to be expressed in the spleen and in various blood cells such as leukocytes, B-cells, and macrophages. The cell affected in accordance with this aspect of the present invention can be one of the above-identified cells or present in one of the above-identified tissues.

It may be desirable to use compounds that are selective for one cannabinoid receptor over another. Compounds selective for the CB-1 receptor, preferably exhibit a $K_i$ ratio [CB1/CB2] that is at least 4:1, more preferably at least 10:1, most preferably at least 20:1. Compounds selective for the CB-2 receptor, preferably exhibit a $K_i$ ratio [CB2/CB1] that is at least 4:1, more preferably at least 10:1, most preferably at least 20:1.

Treatment or prevention of cannabinoid receptor-mediated conditions can be achieved by providing a compound of the present invention and then administering an effective amount of that compound, or a composition containing the same, to a patient for treatment or prevention of the condition.

A number of uses have been identified for modulators of cannabinoid receptors, generally, as well as specifically for CB, receptor agonists, CB, receptor antagonists, $CB_2$ receptor agonists, and $CB_2$ receptor antagonists.

CB receptor modulators have been identified as being useful for treating respiratory diseases (e.g., chronic pulmonary obstructive disorder, emphysema, asthma, bronchitis, etc.) and immunomodulatory diseases or disorders (e.g., transplant rejection, rheumatoid arthritis, multiple sclerosis, inflammatory bowel disease, lupus, graft versus host disease, T-cell mediated hypersensitivity disease, psoriasis, Hashimoto's thyroiditis, Guillain-Barre syndrome, cancer, contact dermatitis, allergic rhinitis, ischemic or reperfusion injury (U.S. Pat. No. 6,653,304 to Leftheris et al., which is hereby incorporated by reference in its entirety).

CB-1 receptor agonists have been identified as being useful for prophylaxis and treatment of neurodegenerative disorders such as cerebral apoplexy and craniocerebral trauma (U.S. Pat. No. 6,284,788 to Mittendorf et al., which is hereby incorporated by reference in its entirety); treatment of hypertension, peripheral vascular disease, angina pectoris, and hemorrhagic shock (U.S. Pat. No. 5,939,429 to Kunos et al., which is hereby incorporated by reference in its entirety); and treatment of cell proliferative disorders (e.g., breast cancer or prostate cancer) (Guzmán, Nature Reviews Cancer 3:745–755 (2003), which is hereby incorporated by reference in its entirety).

CB-1 receptor antagonists have identified as being useful for preventing or treating neuroinflammatory pathologies, particularly conditions involving demyelinization (e.g., multiple sclerosis, Guillain-Barre syndrome), viral encephalitis, cerebrovascular accidents, or cranial trauma (U.S. Pat. No. 6,642,258 to Bourrie et al., which is hereby incorporated by reference in its entirety); ocular disorders such as glaucoma, pulmonary disorders such asthma and chronic bronchitis, allergic diseases such as allergic rhinitis, contact dermatitis, allergic conjunctivitis, inflammation such as arthritis and inflammatory bowel disease, pain, immune system disorders such as lupus and AIDS, allograft rejection, central nervous system diseases such as Tourette's Syndrome, Parkinson's Disease, Huntington's Disease, epilepsy, various psychotic disorders (e.g., depression, manic depression, etc.), and emesis (U.S. Pat. No. 6,509,367 to Martin et al., which is hereby incorporated by reference in its entirety); treating eating disorders such as anorexia and consumption disorders involving consumption of non-essential food items (e.g., sugars, carbohydrates, alcohol, drugs, etc.) (U.S. Pat. No. 6,344,474 to Maruani et al., which is hereby incorporated by reference in its entirety); treating hypotension, such as hypotension associated with septic shock (U.S. Pat. No. 5,939,429 to Kunos et al., which is hereby incorporated by reference in its entirety); treatment of depression, loss of cognitive function, loss of mental alertness, loss of memory, loss of sensory perception associated with one or more of Alzheimer's Disease, head trauma, senile dementia, and brain tumors (U.S. Pat. No. 5,747,524 to Cullinan et al., which is hereby incorporated by reference in its entirety).

CB-2 receptor modulators have been identified as being useful for treatment of cell proliferative disorders such as cancers (U.S. Pat. No. 6,448,288 to Burstein et al, which is hereby incorporated by reference in its entirety).

CB-2 receptor agonists have been identified as being useful for treatment of immunologically-mediated immune disorders such as rheumatoid arthritis, systemic lupus erythematosus, psoriasis, eczema, multiple sclerosis, diabetes, and thyroiditis, bone formation/resorption disorders such as osteoporosis, ankylosing spondylitis, gout, arthritis associated with gout, and osteoarthritis, and renal ischemia (U.S. Pat. No. 6,100,259 to Xiang et al.; U.S. Pat. No. 5,948,777 to Bender et al., each of which is hereby incorporated by reference in its entirety).

Pharmacological activity of the compounds of the present invention (i.e., as agonist, inverse agonist, antagonist, etc.) can be determined using standard in vitro assays that are well known in the art, such as the cyclic AMP or 35S (GTPγS) binding assays (see, e.g., Pertwee, *Curr. Med. Chem.* 6(8):635–664 (1999), which is hereby incorporated by reference in its entirety).

EXAMPLES

The following examples are provided to illustrate embodiments of the present invention but are by no means intended to limit its scope.

Materials and Methods for Examples 1–4

Materials

All chemicals and reagents were purchased from Sigma-Aldrich or Fisher Scientific Inc. Anhydrous solvents were prepared by distillation over sodium metal or calcium hydride just prior to use. All reactions were carried out under dry conditions and under an argon atmosphere. Silica Gel 60, 200–425 mesh was used for flash chromatography. $^1$H NMRs, $^{13}$C NMRs and 2D spectra were obtained on a Varian 500 Inova MHz NMR and were consistent with the assigned structures. All NMR were recorded in CDCl$_3$ unless otherwise specified. Routine mass spectra were determined on a Bruker ESQUIRE Ion Trap LC/MS(n) system while HRMS were measured at the Mass Spectrometry Center, University of Tennessee, Knoxville. IR spectra were measured on a Perkin-Elmer Model 1605 FT infrared spectrophotometer. Thin layer chromatography was performed on silica gel plates (Merck TLC plates, silica gel 60, F$_{254}$).

NMR Studies and Molecular Modeling

All spectra were acquired at 23° C. and 500 MHz on a Varian Inova-500 spectrometer using a 5-mm HCN triple resonance probe. Both proton and carbon chemical shifts were referenced to the residual solvent peak of DMSO (2.49 ppm for proton and 40 ppm for carbon). For two-dimensional NOESY measurements, a total of 512 fids were recorded for the indirect dimension, with a 2 second recycle delay. The TRIAD NMR package within the Sybyl software was used for data processing and analysis. Peaks in the NOESY spectra were assigned and integrated using TRIAD standard functions. MARDIGRAS was then used to generate distance constraints for 28 using these peak integrals. Results from each of the five mixing times gave very similar distance constraints, hence each distance constraint was averaged over the five mixing times to get the final set of distance constraints for the molecule. The resulting constraints were then examined to ensure that the error in distances conformed to established errors for NOE constraints wherein; x<2.5 Å was +/−0.1 Å; x≦3.0 Å was +/−0.2 Å; x≦3.5 Å was +/−0.3 Å; and x≧3.5 was +/−0.4 Å.

A four-step simulated annealing using 1 fs time steps and the constraints generated by MARDIGRAS was performed on 28 as follows: (1) 1 ps dynamics at 300K; (2) 1 ps heating to 500K; (3) another 1 ps heating phase to 700K; (4) a 1 ns equilibration to 500K. Additional parameters included the Tripos force field with Gasteiger-Hückel charges, an 8 Å nonbonding cutoff, and distance dependent dielectric constant function. The experimentally obtained NOE distance constraints were applied during all steps of the dynamics runs, and the aromatic carbons were defined as aggregates to maintain the ring geometry. The molecular geometry was sampled at 1000 fs intervals during phase (1) of the dynamics runs and once during the heating and cooling periods. A total of 1,007 conformations were collected during for further analysis and these were subjected to twenty dynamics simulations each to obtain average conformations. These average conformations were then minimized with a gradient tolerance of 0.005 Kcal·mol$^{-1}$. Å$^{-1}$ without defined aggregates or experimental NOE distance constraints to obtain the final average conformations.

Quantum Mechanical Calculations

Quantum mechanical calculations were performed using the GAMESS computational chemistry package on a SGI Origin 2000 with 8 processors and 4 GB of memory. Molecular orbital surfaces were calculated from the B3LYP/6-31G(p,d) results using a version of MOLDEN (Schaftenaar, G. et al., *J. Comput.-Aided Mol. Design* 14:123 (2000), which is hereby incorporated by reference in its entirety) modified at the University of Memphis. Potential energy surfaces were calculated using the AM1 and PM3 semi-empirical wavefunctions, as were the final geometries optimizations.

Receptor Binding Assays

Cell membranes from HEK293 cells transfected with the human CB1 receptor (Lot #1929, B$_{max}$: 1.7 pmol/mg protein, K$_d$ for [$^3$H]CP 55,940 binding: 186 pM) and membranes from CHO-K1 cells transfected with the human CB2 receptor (Lot #1930, B$_{max}$: 3.3 pmol/mg protein, K$_d$ for [$^3$H]CP 55,940 binding: 0.12 nM) were purchased from Perkin-Elmer Life Sciences, Inc. [$^3$H]CP 55,940 having a specific activity of 120 Ci/mmol was obtained from Perkin-Elmer Life Sciences, Inc. All other chemicals and reagents were obtained from Sigma-Aldrich. The assays were carried out in 96 well plates obtained from Millipore, Inc. fitted with glass fiber filters (hydrophilic, GFC filters) having a pore size of 1.2 μ. The filters were soaked with 0.05% polyethyleneimine solution and washed 5× with deionized water prior to carrying out the assays. The filtrations were carried out on a 96 well vacuum manifold (Millipore Inc.), the filters punched out with a pipette tip directly into scintillation vials at the end of the experiment and vials filled with 5 ml scintillation cocktail Ecolite (+)(Fisher Scientific). Counting was carried out on a Beckmann Scintillation Counter model LS6500. Drug solutions were prepared in DMSO and the radioligand was dissolved in ethanol.

The incubation buffer contained 50 mM TRIS-HCl, 5mM MgCl$_2$, 2.5 mM EDTA, 0.5 mg/ml fatty acid free bovine serum albumin, pH 7.4.

The binding protocol for the CB1 receptor is set forth below: 8 μg of membranes (20 μl of a 1:8 dilution in incubation buffer) was incubated with 5 μl of drug solution (10$^{-4}$M to 10$^{-12}$M) and 5 μl of 5.4 nM [$^3$H]CP 55,940 in a total volume of 200 μl for 90 mins at 30 C. Non-specific binding was determined using 10 μM WIN55,212-2 (K$_i$=4.4 nM). The membranes were filtered and the filters washed 7× with 0.2 ml ice-cold incubation buffer and allowed to air dry under vacuum.

The binding protocol for the CB2 receptor is set forth below: 15.3 μg of membranes (20 μl of a 1:20 dilution in incubation buffer) was incubated with 5 μl of drug solution (10$^{-4}$M to 10$^{-12}$M) and 5 μl of 10 nM [$^3$H]CP 55,940 in a total volume of 200 μl for 90 mins at 30 C. Non-specific binding was determined using 10 μM WIN55,212-2 (K$_i$=4.4 nM). The membranes were filtered and the filters washed 7× with 0.2 ml ice-cold incubation buffer and allowed to air dry under vacuum.

Data accumulation and statistical analysis was carried out as follows: Varying concentrations of drug ranging from $10^{-4}$M to $10^{-12}$M were added in triplicate for each experiment and the individual molar IC$_{50}$ values were determined using GraphPad Prism. The corresponding K$_i$ values for each drug were determined utilizing the Cheng and Prusoff equation (Cheng, Y. et al., *Biochem. Pharmacol.* 22:3099 (1973), which is hereby incorporated by reference in its entirety) and final data are presented as K$_i$±S.E.M. of n≧2 experiments.

Example 1

Synthesis of Δ$^8$-THC Analogs Containing 1'-Cycloalkane Functionality

Figure 7:
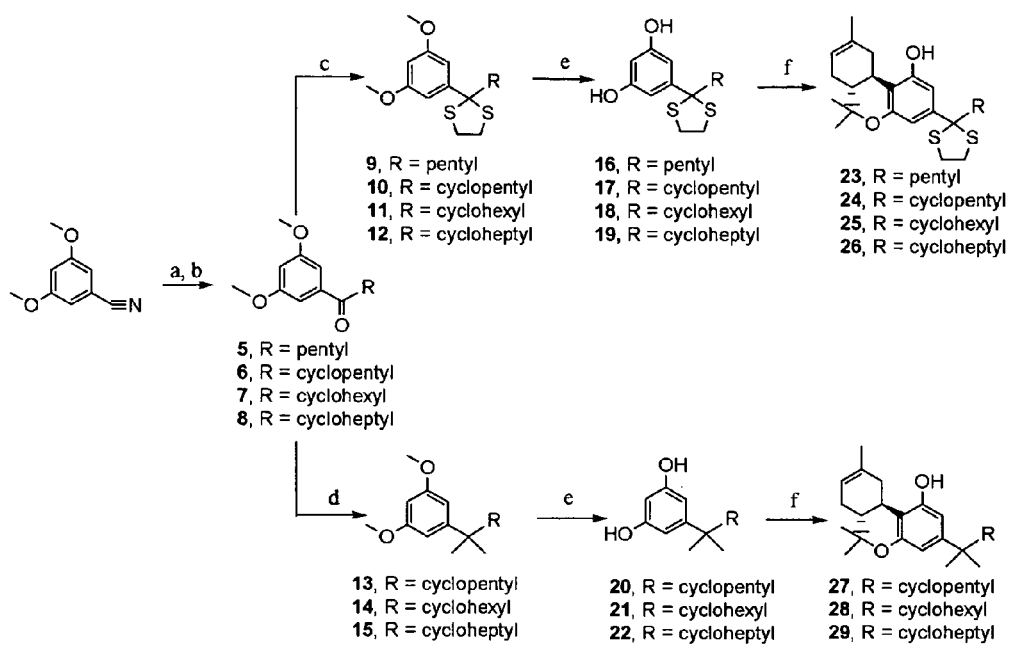
FIG. 7 illustrates a synthesis scheme used to prepare various $\Delta^8$-THC analogs of the present invention having a 1'-cycloalkyl substituent.

The synthesis of the side chain modified analogs of Δ$^8$-THC was carried out by the acid catalyzed coupling of cis-Δ$^2$-p-menthene-1,8-diol with the appropriately substituted resorcinol (Papahatjis, D. P. et al., *J. Med. Chem.* 41:1195 (1998), which is hereby incorporated by reference in its entirety). The precursor resorcinols were synthesized as summarized in FIG. 7, by reacting 3,5-dimethoxybenzonitrile with the Grignard of the appropriate alkyl or cycloalkyl halide followed by HCl hydrolysis of the resulting imine to yield ketones 5–8 (Singer, M. et al., *J. Med. Chem.* 41:4400 (1998), which is hereby incorporated by reference in its entirety). These ketones were then reacted with either ethane-1,2-dithiol in the presence of BF$_3$.Et$_2$O to give the corresponding dithiolanes 9–12 (Papahatjis, D. P. et al., *J. Med. Chem.* 41:1195 (1998), which is hereby incorporated by reference in its entirety) or reacted with dimethylzinc and TiCl$_4$ thus yielding the corresponding gem-dimethyl intermediates 13–15 (Singer, M. et al., *J. Med. Chem.* 41:4400 (1998), which is hereby incorporated by reference in its entirety). Deprotection of the intermediate aryl ethers using BBr$_3$ at 0° C. for 12–16 hours generated the 5-substituted resorcinols 16–22. Reaction of the resorcinols with cis-Δ$^2$-p-menthene-1,8-diol, prepared from (+)-Δ$^2$-carene according to the method of Prasad and Dev (Prasad, R. S. et al., *Tetrahedron* 32:1437 (1976), which is hereby incorporated by reference in its entirety), in the presence of p-toluenesulphonic acid monohydrate gave the corresponding Δ$^8$-THC analogs 23–29.

Compound 5:1-(3,5-Dimethoxy-phenyl)-pentan-1-one

To Mg turnings (1.12 g, 46.7 mmol), dried in an oven for 1 hour, and dry THF (32 ml) was added 1-butylbromide (4.46 g, 32.5 mmol) and allowed to react at reflux for half an hour. After formation of the Grignard, 3,5-dimethoxybenzonitrile (4 g, 24.5 mmol) was added and the mixture was refluxed for 4 h. The reaction was cooled with ice for 15 minutes followed by the slow addition of 40 ml of 6N HCl and then the mixture was refluxed for 16 h. The THF was removed and the residue dissolved in EtOAc (60 ml) and 6N HCl (15 ml). The layers were separated, the aqueous layer extracted with EtOAc (4×20 ml). The combined EtOAc extracts were extracted and washed with saturated NaHCO$_3$, water and brine. After drying the organic phase was concentrated and the residue resolved on silica gel eluting with EtOAc/hexanes (5:25), to yield 3.52 g (64.7%) of compound 5 as a white solid. R$_f$=0.43 (Hexane:ethyl acetate 9:1); IR (KBr pellet) 2956, 1601, 1206, 1067, 755 cm$^{-1}$; $^1$H NMR δ 7.09 (d, J=2.31 Hz, 2H), 6.64 (t, J=2.31 Hz, 1H), 3.84 (s, 6H), 2.92 (t, J=7.4 Hz, 2H), 1.71 (q, J=7.71 Hz, 2H), 1.40 (s, J=7.71 Hz, 2H), 0.95 (t, J=7.32 Hz, 3H); $^{13}$C NMR δ 200.51, 161.10, 139.33, 106.17, 105.29, 55.83, 38.70, 26.84, 22.71, 14.17; MS: (ESI, Pos.) m/z 245 ([M+23]$^+$).

Compound 6:
Cyclopentyl-(3,5-dimethoxy-phenyl)-methanone

Using the appropriate alkylbromide, Compound 6 was similarly prepared from 3,5-dimethoxybenzonitrile as described with respect to Compound 5.

Yield 2.90 g (50.2%) as a clear oil. R$_f$=0.58 (hexane:ethyl acetate 9:1); IR (KBr neat) 2956, 1604, 1204, 1067, 755cm$^-$$_1$; $^1$H NMR δ 7.11 (d, J=2.31 Hz, 2H), 6.63 (t, J=2.29 Hz, 1H), 3.83 (s, 6H), 3.70–3.60 (m, 1H), 1.95–1.87 (m, 4H), 1.75–1.59 (m, 4H); $^{13}$C NMR δ 202.71, 161.06, 139.23, 106.57, 105.11, 55.80, 46.72, 30.35, 26.54; MS: (ESI, Pos.) m/z 257 ([M+23]$^+$).

Compound 7:
Cyclohexyl-(3,5-dimethoxy-phenyl)-methanone

Using the appropriate alkylbromide, Compound 7 was similarly prepared from 3,5-dimethoxybenzonitrile as described with respect to Compound 5.

Yield 19.3 g (63.3%) as a clear oil. R$_f$=0.43 (hexane:ethyl acetate 9: 1); IR (KBr neat) 2936, 1594, 1200, 1059, 734 cm$^{-1}$; $^1$H NMR δ 7.08 (d, J=2.4 Hz, 2H), 6.63 (t, J=2.25 Hz, 1H), 3.83 (s, 6H), 3.24–3.14 (m, 1H), 2.05–1.71 (m, 5H), 1.54–1.19 (m, 5H); $^{13}$C NMR δ 203.73, 161.12, 138.61, 106.35, 104.92, 55.77, 45.99, 30.39, 29.73, 27.12, 26.17, 26.05; MS: (ESI, Pos.) m/z 271 ([M+23]$^+$).

Compound 8:
Cycloheptyl-(3,5-dimethoxy-phenyl)-methanone

Using the appropriate alkylbromide, Compound 8 was similarly prepared from 3,5-dimethoxybenzonitrile as described with respect to Compound 5.

Yield 11.0 g (45.6%) as a clear oil. R$_f$=0.58 (hexane:ethyl acetate 9:1); IR (KBr neat) 2941, 1592, 1201, 1063, 757 cm$^{-1}$; $^1$H NMR δ 7.07 (d, J=2.4 Hz, 2H), 6.64 (t, J=2.4 Hz, 1H), 3.84 (s, 6H), 3.40–3.32 (m, 1H), 1.96–1.52 (m, 12H). $^{13}$C NMR δ 204.16, 161.12, 138.72, 106.40, 104.96, 55.80, 46.99, 46.66, 31.59, 31.13, 28.55, 28.36, 28.08, 27.04; MS: (ESI, Pos.) m/z 285 ([M+23]$^+$).

Compound 9:
2-Butyl-2-(3,5-dimethoxy-phenyl)-[1,3]dithiolane

To a stirred solution of Compound 5 (3.52 g, 15.9 mmol) in anhydrous CH$_2$Cl$_2$ (58 ml); was added BF$_3$-Et$_2$O (0.58 ml, 4.8 mmol) and ethane-1,2-dithiol (2.71 g, 28.8 mmol) and stirred at room temperature for 16 h. The organic phase was then extracted with 10% NaOH (20 ml) followed by water and brine. The organic phase was dried, concentrated and the residue resolved over silica gel eluting with EtOAc/hexanes (5:10) to yield 4.50 g (95.2%) of Compound 9 as a colorless oil. R$_f$=0.51 (hexane:ethyl acetate 9:1); IR (neat) 2955, 1205, 1067 694 cm$^{-1}$; $^1$H NMR δ 6.89 (d, J=2.22 Hz, 2H), 6.34 (t, J=2.21 Hz, 1H), 3.81 (s, 6H). 3.40–3.20 (m, 4H), 2.33 (t, J=7.53 Hz, 2H), 1.31–1.20 (m, 4H), 0.85 (t, J=6.78 Hz, 3H). $^{13}$C NMR δ 160.56, 148.04, 106.01, 98.74, 74.58, 55.60, 45.92, 39.33, 30.23, 23.03, 14.13; MS: (ESI, Pos.) m/z 299 (M$^+$).

Compound 10: 2-Cyclopentyl-2-(3,5-dimethoxy-phenyl)-[1,3]dithiolane

Compound 10 was prepared from Compound 6 using the same procedure as described above for Compound 9. Yield 2.92 g (87%) as an oil. $R_f$=0.52 (hexane:ethyl acetate 92:8); IR (neat) 2955, 1206, 1066, 694 cm$^{-1}$; $^1$H NMR δ 6.98 (d, J=2.19 Hz, 2H), 6.34 (t, J=2.25 Hz, 1H), 3.80 (s, 6H), 3.35–3.09 (m, 4H), 2.82–2.71 (m, 1H), 1.80–1.43 (m, 8H). $^{13}$C NMR δ 160.03, 149.37, 106.37, 98.35, 79.474, 55.35, 52.14, 38.79, 31.17, 25.73; MS: (ESI, Pos.) m/z 333 ([M+23]$^+$).

Compound 11: 2-Cyclohexyl-2-(3,5-dimethoxy-phenyl)-[1,3]dithiolane

Compound 11 was prepared from Compound 7 using the same procedure as described above for Compound 9. Yield 16.8 g (89.6%) as an oil. $R_f$=0.43 (hexane:ethyl acetate 92:8); IR (neat) 2930, 1198, 1062, 698 cm$^{-1}$; $^1$H NMR δ 6.94 (d, J=2.4 Hz, 2H), 6.33 (t, J=2.25 Hz, 1H), 3.80 (s, 6H), 3.33–3.09 (m, 4H), 2.17–2.09 (m, 1H), 1.92–1.88 (m, 2H), 1.73–1.58 (m, 3H), 1.27–0.97 (m, 5H). $^{13}$C NMR δ 160.20, 148.17, 107.00, 98.59, 80.97, 55.60, 50.71, 39.07, 31.18, 26.91, 26.35; MS: (ESI, Pos.) m/z 347 ([M+23]$^+$).

Compound 12: 2-Cycloheptyl-2-(3,5-dimethoxy-phenyl)-[1,3]dithiolane

Compound 12 was prepared from Compound 8 using the same procedure as described above for Compound 9. Yield 3.60 g (79.2%) as an oil. $R_f$=0.56 (hexane:ethyl acetate 92:8); IR (neat) 2925, 1206, 1067, 832, 693 cm$^{-1}$; $^1$H NMR δ 6.94 (d, J=2.4 Hz, 2H), 6.32 (t, J=2.25 Hz, 1H), 3.80 (s, 6H), 3.31–3.10 (m, 4H), 2.40–2.32 (m, 1H), 1.96–1.30 (m, 12H). $^{13}$C NMR δ 160.38, 148.94, 106.52, 98.48, 81.99, 70.21, 55.60, 51.27, 45.22, 39.34, 32.82, 29.80, 28.04, 27.77; MS: (ESI, Pos.) m/z 361 ([M+23]$^+$).

Compound 13: 1-(1-Cyclopentyl-1-methyl-ethyl)-3,5-dimethoxy-benzene

In a dry three-necked flask equipped with an addition funnel was added anhydrous CH$_2$Cl$_2$ (80 ml) and cooled to –40° C. A 1 M solution of TiCl$_4$ in CH$_2$Cl$_2$ (102 ml, 102 mmol) was transferred to the addition funnel and added slowly to the cold CH$_2$Cl$_2$ solution maintaining a temperature of –40° C. The solution was cooled to –50° C. and via the addition funnel a 2 M solution of dimethylzinc in toluene (51 ml, 102 mmol) was added as rapidly as possible, maintaining the temperature between –40 and –50° C. Upon completion of the addition, the viscous red solution was stirred vigorously for 10 min, after which a solution of Compound 6 (4.01 g, 17.1 mmol) in dry CH$_2$Cl$_2$ (20 ml) was added rapidly maintaining the temperature between –45 and –35° C. The temperature was then allowed to rise slowly to –10° C. over 2 hrs with constant stirring. The mixture was poured into ice/water (200 ml) and the aqueous layer was extracted with CH$_2$Cl$_2$ (4×50 ml). The combined organic extracts were washed with saturated NaHCO$_3$, water and brine, dried and concentrated. The residue was resolved over silica gel EtOAc/hexanes (1:9) to yield 2.75 g (65.0%) of Compound 13 as a colorless oil. $R_f$=0.50 (hexane:ethyl acetate 95:5); IR (neat) 2955, 1457, 1422, 1205, 1067, 831 cm$^{-1}$; $^1$H NMR δ 6.53 (d, J=2.4 Hz, 2H), 6.30 (t, J=2.25, 1H), 3.79 (s, 6H), 1.55–1.38 (m, 7H), 1.25 (s, 6H), 1.21–1.15 (m, 2H); $^{13}$C NMR δ 160.50, 153.36, 105.30, 96.76, 55.45, 51.80, 39.90, 27.94, 25.97, 25.82; MS: (ESI, Pos.) m/z 249 ([M+H]$^+$).

Compound 14: 1-(1-Cyclohexyl-1-methyl-ethyl)-3,5-dimethoxy-benzene

Compound 14 was prepared from Compound 7 using the same procedure as described above for Compound 13. Yield 3.69 g (70.3%) as an oil. $R_f$=0.55 (hexane:ethyl acetate 95:5); IR (neat) 2932, 1457, 1422, 1208, 1066 702 cm$^{-1}$; $^1$H NMR δ 6.48 (d, J=2.4 Hz, 2H), 6.35 (t, J=2.1 Hz, 1H), 3.80 (s, 6H), 1.72–1.55 (m, 6H), 1.45–1.39 (m, 1H), 1.21 (s, 6H), 1.18–1.05 (m, 2H), 0.97–0.85 (m, 2H); $^{13}$C NMR δ 160.52, 153.48, 105.35, 96.64, 55.44, 49.28, 41.06, 28.18, 27.44, 26.96, 25.50; MS: (ESI, Pos.) m/z 263 ([M+H]$^+$).

Compound 15: 1-(1-Cycloheptane-1-methyl-ethyl)-3,5-dimethoxy-benzene

Compound 15 was prepared from Compound 8 using the same procedure as described above for Compound 13. Yield 3.61 g (72.3%) as an oil. $R_f$=0.50 (hexane:ethyl acetate 95:5) IR (neat) 2934, 1455, 1422, 1206, 1067, 701 cm$^{-1}$; $^1$H NMR δ 6.50 (d, J=2.5 Hz, 2H), 6.29 (t, J=2.25 Hz, 1H), 3.80 (s, 6H), 1.73–1.69 (m, 1H), 1.65–1.50 (m, H), 1.48–1.38 (m, H), 1.37–1.28 (m, H), 1.18 (s, 6H); $^{13}$C NMR δ 160.33, 153.83, 104.94, 96.41, 55.21, 49.21, 42.03, 29.52, 28.06, 27.95, 25.19; MS: (ESI, Pos.) m/z 277 ([M+H]$^+$).

Compound 16: 5-(2-Butyl-[1,3]dithiolan-2-yl)-benzene-1,3-diol

Boron tribromide (32.9 ml of 1M soln, 32.9 mmol) was added to a solution of Compound 9 (4.51 g, 3.23 mmol) in CH$_2$Cl$_2$ (546 ml) under argon at –78° C. The reaction temperature was then raised slowly to 0° C. over a period of 3 hrs. Stirring was continued at 0° C. for 12–14 hrs or until completion of reaction. Unreacted boron tribromide was destroyed by adding methanol, solvent removed and the residual oil diluted with diethyl ether. The organic phase was washed with saturated NaHCO$_3$, water and brine, dried and concentrated. The residue was resolved over silica gel eluting with diethylether/hexanes (4:6) to yield 0.675 g (74.1%) of Compound 16 as a waxy solid. $R_f$=0.28 (hexane:ethyl acetate 8:2) $^1$H NMR δ 6.79 (d, J=2.5 Hz, 2H), 6.23 (t, J=2H, 1H), 5.30 (br s, 2H), 3.38–3.19 (m, 4H), 2.25 (t, J=9.75 Hz, 2H), 1.29–1.18 (m, 4H), 0.83 (t, J=7 Hz, 3H); $^{13}$C NMR δ 156.24, 148.45, 107.23, 101.50, 73.90, 45.50, 39.01, 29.96, 22.74, 13.86; MS: (ESI, Neg.) m/z 269 ([M–H]$^-$).

Compound 17: 5-(2-Cyclopentyl-[1,3]dithiolan-2-yl)-benzene-1,3-diol

Compound 17 was prepared from Compound 10 using the same procedure as described above for Compound 16. Yield 0.67 g (74.1%) as a waxy solid. $R_f$=0.28 (hexane:ethyl acetate 8:2); $^1$H NMR δ 6.89 (d, J=2.4 Hz, 2H), 6.23 (t, J=2.1 Hz, 1H), 5.68 (br s, 2H), 3.34–3.07 (m, 4H), 2.78–2.67 (m, 1H), 1.71–1.38 (m, 8H); $^{13}$C NMR δ 156.26, 150.31, 108.13, 101.59, 79.28, 52.27, 39.02, 31.39, 25.94; MS: (ESI, Pos.) m/z 305 ([M+23]$^+$).

Compound 18: 5-(2-Cyclohexyl-[1,3]dithiolan-2-yl)-benzene-1,3-diol

Compound 18 was prepared from Compound 11 using the same procedure as described above for Compound 16. Yield 0.853 g (62.2%) as a waxy solid. $R_f$=0.27 (hexane:ethyl acetate 8:2); $^1$H NMR δ 6.78 (d, J=0.9 Hz, 2H), 6.19 (t, J=1.95 Hz, 1H), 4.14 (br s, 2H), 3.32–3.07 (m, 4H), 2.15–2.06 (m, 1H), 1.96–1.58 (m, 4H), 1.19–1.00 (m, 4H); $^{13}$C NMR δ 156.95, 147.94, 107.39, 101.12, 80.58, 60.83, 50.56, 38.82, 30.92, 26.77, 26.24, 21.08, 14.17; MS: (ESI, Neg.) m/z 295 ([M–H]$^-$).

Compound 19: 5-(2-Cycloheptyl-[1,3]dithiolan-2-yl)-benzene-1,3-diol

Compound 19 was prepared from Compound 12 using the same procedure as described above for Compound 16. Yield 0.582 g (41.5%) as a waxy solid. $R_f$=0.28 (hexane:ethyl acetate 8:2); $^1$H NMR δ 6.85 (d, J=2.4 Hz, 2H), 6.22 (t, J=2.25 Hz, 1H), 5.16 (br s, 2H), 3.31–3.07 (m, 4H), 2.35–2.28 (m, 1H), 1.97–1.29 (m, 12H); $^{13}$C NMR δ 156.07, 149.33, 107.65, 101.25, 50.92, 39.00, 32.55, 27.70, 27.43; MS: (ESI, Pos.) m/z 333 ([M+23]$^+$).

Compound 20: 5-(1-Cyclopentyl-1-methyl-ethyl)-benzene-1,3-diol

Compound 20 was prepared from Compound 13 using the same procedure as described above for Compound 16. Yield 1.29 g (72.9%) as a viscous oil. $R_f$=0.28 (hexane:diethyl ether 6:4); $^1$H NMR δ 6.44 (d, J=2.1 Hz, 2H), 6.20 (t, J=2.1 Hz, 1H), 5.70 (br s, 2H), 2.02–1.98 (m, 1H), 1.57–1.35 (m, 6H), 1.18 (s, 6H); $^{13}$C NMR δ 156.22, 154.66, 105.10, 99.83, 53.24, 50.33, 36.21, 24.99, 24.75; MS: (ESI, Neg.) m/z 219 ([M–H]$^-$).

Compound 21: 5-(1-Cyclohexyl-1-methyl-ethyl)-benzene-1,3-diol

Compound 21 was prepared from Compound 14 using the same procedure as described above for Compound 16. Yield 1.11 g (61.9%) as a viscous oil. $R_f$=0.28 (hexane:diethyl ether 6:4); $^1$H NMR δ 6.38 (d, J=2 Hz, 2H), 6.17 (t, J=2.25 Hz, 1H), 4.82 (br s, 2H), 1.71–1.68 (m, 2H), 1.63–1.60 (m, 1H), 1.53–1.51 (m, 2H), 1.42–1.36 (m, 1H), 1.17 (s, 6H), 1.16–1.03(m, 3H), 0.94–0.86 (m, 2H); $^{13}$C NMR δ 156.32, 154.45, 106.56, 100.02, 49.21, 40.85, 28.12, 27.39, 26.91, 25.39, 14.40; MS: (ESI, Neg.) m/z 233 ([M–H]$^-$).

Compound 22: 5-(1-Cycloheptyl-1-methyl-ethyl)-benzene-1,3-diol

Compound 22 was prepared from Compound 15 using the same procedure as described above for Compound 16. Yield 0.442 g (24.7%) as a viscous oil. $R_f$=0.26 (hexane:diethyl ether 6:4); $^1$H NMR δ 6.40 (d, J=2 Hz, 2H), 6.17 (t, J=2 Hz, 1H), 4.74 (br s, 2H), 1.68–1.50 (m, 7H), 1.48–1.39 (m, 2H), 1.35–1.25 (m, 2H), 1.15 (s, 6H), 1.14–1.08 (m, 2H); $^{13}$C NMR δ 156.15, 154.78, 106.13, 99.74, 49.22, 41.79, 29.46, 28.01, 27.88, 25.06; MS: (ESI, Neg.) m/z 247 ([M–H]$^-$).

Compound 23: 3-(2-Butyl-[1,3]dithiolan-2-yl)-6,6,9-trimethyl-6a,7,10,10a-tetrahydro-6H-benzo[c]chromen-1-ol To a solution of Compound 16 (650 mg, 2.4 mmol) in dry benzene (20 ml) was added cis-Menth-2-ene-1,8-diol (408 mg, 2.4 mmol) followed by the addition of p-toluenesulfonic acid monohydrate (19 mg, 0.099 mmol). The reaction mixture was stirred at 80° C. for 4 hours. The reaction mixture was cooled and diluted with ether and washed well with saturated NaHCO$_3$, water and brine. After drying it was concentrated and the residue resolved on silica gel (1.9 cm×25 cm), eluting with 3% diethylether-petroleum ether to yield 254 mg (26.3%) of Compound 23 as a light yellow, waxy solid. $R_f$=0.22 (petroleum ether:diethyl ether 9:1) $^1$H NMR δ 6.77 (d, J=2 Hz, 1H), 6.63 (d, J=1.5 Hz, 1H), 5.44 (d, J=4 Hz, 1H), 4.82 (s, 1H), 3.37–3.24 (m, 4H), 3.22–3.18 (m, 1H), 2.73–2.68 (m, 1H), 2.31–2.27 (m, 2H), 2.17–2.18 (m, 1H), 1.86–1.79 (m, 3H), 1.71 (s, 3H), 1.40 (s, 3H), 1.29–1.23 (m, 6H), 1.12 (s, 3H), 0.86–0.84 (m, 3H); $^{13}$C NMR δ 154.81, 154.65, 144.23, 134.95, 119.53, 112.11, 109.55, 106.69, 77.17, 73.98, 45.87, 44.97, 39.40, 37.11, 36.03, 31.83, 30.18, 28.09, 27.81, 23.73, 23.04, 18.80, 14.17; HRMS (FAB), m/z, calculated for $C_{23}H_{32}O_2S_2$, 404.1844, experimental 404.1844.

Compound 24: dithiolanyl-cyclopentyl Δ$^8$-THC or 3-(2-Cyclopentyl-[1,3]dithiolan-2-yl)-6,6,9-trimethyl-6a,7,10,10a-tetrahydro-6H-benzo[c]chromen-1-ol Compound 24 was prepared from Compound 17 using the same procedure as described above for Compound 23. Yield 55 mg (14.6%) as a light yellow, waxy solid. $R_f$=0.22 (petroleum ether:diethyl ether 9:1) $^1$H NMR δ 6.86 (d, J=1.5 Hz, 1H), 6.70 (d, J=2Hz, 1H), 5.43 (d, J=4Hz, 1H), 4.76 (br s, 1H), 3.33–3.12 (m, 5H), 2.77–2.66 (m, 1H), 2.15–2.12 (m, 1H), 1.88–1.78 (m, 3H), 1.70 (s, 3H), 1.68–1.67 (m, 2H), 1.60–1.59 (m, 3H), 1.53–1.42 (m, 5H), 1.38 (s, 3H), 1.10 (s, 3H); $^{13}$C NMR δ 154.55, 154.33, 146.82, 134.95, 119.53, 111.90, 110.12, 107.31, 79.00, 52.40, 44.98, 39.12, 36.06, 31.83, 31.41, 31.34, 28.08, 27.80, 25.91, 23.71, 18.77; HRMS (FAB), m/z, calculated for $C_{24}H_{32}O_2S_2$, 416.1844, experimental 416.1841.

Compound 25: dithiolanyl-cyclohexyl Δ$^8$-THC or 3-(2-Cyclohexyl-[1,3]dithiolan-2-yl)-6,6,9-trimethyl-6a,7,10,10a-tetrahydro-6H-benzo[c]chromen-1-ol Compound 25 was prepared from Compound 18 using the same procedure as described above for Compound 23. Yield 193 mg (22.2%) as a light yellow solid. $R_f$=0.22 (petroleum ether:diethyl ether 9:1) $^1$H NMR δ 6.81 (d, J=2 Hz, 1H), 6.65 (d, J=2 Hz, 1H), 5.44 (d, J=5 Hz, 1H), 4.79 (br s, 1H), 3.28–3.10 (m, 5H), 2.72–2.66 (m, 1H), 2.16–2.06 (m, 2H), 1.93–1.79 (m, 5H), 1.72–1.67 (m, 1H), 1.70 (s, 3H), 1.61–1.58 (m, 1H), 1.29–1.02 (m, 6H), 1.38 (s, 3H), 1.11 (s, 3H); $^{13}$C NMR δ 154.48, 154.25, 145.36, 134.97, 119.54, 111.94, 110.44, 107.62, 80.35, 77.11, 66.14, 50.61, 44.99, 39.14, 36.07, 31.85, 31.07, 31.00, 28.10, 27.83, 26.88, 26.36, 23.74, 18.81, 15.50, 11.94; HRMS (FAB), m/z, calculated for $C_{25}H_{34}O_2S_2$, 430.2000, experimental 430.2000.

Compound 26: dithiolanyl-cycloheptyl Δ$^8$-THC or 3-(2-Cycloheptyl-[1,3]dithiolan-2-yl)-6,6,9-trimethyl-6a,7,10,10a-tetrahydro-6H-benzo[c] chromen-1-ol Compound 26 was prepared from Compound 19 using the same procedure as described above for Compound 23. Yield 61 mg (14.2%) as a light yellow solid. $R_f$=0.22 (petroleum ether:diethyl ether 9:1) $^1$H NMR δ 6.82 (d, J=1.5 Hz, 1H), 6.67 (d, J=1.5 Hz, 1H), 5.426 (d, J=4.5 Hz, 1H), 4.88 (br s, 1H), 3.28–3.11 (m, 5H), 2.72–2.66 (m, 1H), 2.33–2.28 (m, 1H), 2.16–2.13 (m, 1H), 1.93–1.79 (m, 7H), 1.70 (s, 3H), 1.39 (s, 3H), 1.11 (s, 3H), 1.93–1.28 (m, 8H); $^{13}$C NMR δ 154.32, 154.18, 145.80, 134.69, 119.25, 111.59, 109.66, 106.87, 81.16, 76.85, 50.93, 44.67, 39.06, 35.78, 32.54, 32.47, 31.57, 27.78, 27.71, 27.54, 27.48, 23.46, 18.52; HRMS (FAB), m/z, calculated for $C_{26}H_{36}O_2S_2$, 444.2157, experimental 444.2170.

Compound 27: gem-dimethyl-cyclopentyl Δ$^8$-THC or 3-(1-Cyclopentyl-1-methyl-ethyl)-6,6,9-trimethyl-6a,7,10,1a-tetrahydro-6H-benzo[c]chromen-1-ol Compound 27 was prepared from Compound 20 using the same procedure as described above for Compound 23. Yield 334 mg (41.6%) as a light yellow solid. $R_f$=0.32 (petroleum ether:diethyl ether 95:5); $^1$H NMR δ 6.42 (d, J=1 Hz, 1H), 6.26 (d, J=2 Hz, 1H), 5.43(d, J=5 Hz, 1H), 4.66 (br s, 1H), 3.21–3.17 (m, 1H), 2.72–2.67(m, 1H), 2.16–2.13 (m, 1H), 2.06–1.99 (m, 1H), 1.94–1.76 (m, 6H), 1.70 (s, 3H), 1.39 (s, 3H), 1.22–1.13 (m, 2H), 1.11 (s, 3H), 1.18 (s, 6H); $^{13}$C NMR δ 154.8, 154.45, 150.68, 135.00, 119.58, 110.38, 108.60, 106.03, 76.90, 51.77, 45.11, 39.22, 36.25, 31.75, 28.13, 27.90, 27.86, 25.85, 25.76, 23.74, 18.76; HRMS (FAB), m/z, calculated for $C_{24}H_{34}O_2$, 354.2558, experimental 354.2566.

Compound 28: gem-dimethyl-cyclohexyl Δ$^8$-THC or 3-(1-Cyclohexyl-1-methyl-ethyl)-6,6,9-trimethyl-6a,7,10,10a-tetrahydro-6H-benzo[c]chromen-1-ol Compound 28 was prepared from Compound 21 using the same procedure as described above for Compound 23. Yield 298 mg (37.9%) as a light yellow solid. $R_f$=0.33 (petroleum ether:diethyl ether 95:5) $^1$H NMR δ 6.37 (d, J=2 Hz 1H), 6.22 (d, J=1.5 Hz, 1H), 5.43 (d, J=5 Hz, 1H), 4.65(br s, 1H), 3.21–3.17 (m, 1H), 2.72–2.67(m, 1H), 2.18–2.13 (m, 1H), 1.91–1.77 (m, 3H), 1.71 (s, 3H), 1.67–1.67 (m, 2H), 1.61–1.50 (m, 4H), 1.39 (s, 3H), 1.41–1.36 (m, 1H), 1.16 (s, 3H), 1.15 (s, 3H), 1.10–1.03 (m, 3H), 0.92–0.75 (m, 2H); $^{13}$C NMR δ 154.32, 154.23, 150.54, 134.76, 119.34, 110.08, 108.44, 105.80, 76.66, 48.84, 44.87, 40.155, 36.03, 31.51, 27.89, 27.63, 27.18, 26.72, 25.26, 24.93, 23.50, 18.53; HRMS (FAB), m/z, calculated for $C_{25}H_{36}O_2$, 368.2715, experimental 368.2715.

Compound 29: gem-dimethyl-cycloheptyl Δ$^8$-THC or 3-(1-Cycloheptyl-1-methyl-ethyl)-6,6,9-trimethyl-6a,7,10,10a-tetrahydro-6H-benzo[c]chromen-1-ol Compound 29 was prepared from Compound 22 using the same procedure as described above for Compound 23. Yield 341 mg (42.9%) as a light yellow waxy solid. $R_f$=0.33 (petroleum ether:diethyl ether 95:5) $^1$H NMR δ 6.39 (d, J=1.5 Hz, 1H), 6.2 (d, J=1.5 Hz, 1H), 5.43 (d, J=4.5 Hz, 1H), 4.67 (br s, 1H), 3.21–3.17 (m, 1H), 2.72–2.67 (m, 1H), 2.16–2.10 (m, 1H), 1.91–1.79 (m, 3H), 1.70 (s, 3H), 1.67–1.51 (m, 8H), 1.47–1.41 (m, 2H), 1.38–1.26 (m, 3H), 1.14 (s, 6H), 1.11 (s, 3H), 1.12–1.07(m, 1H); $^{13}$C NMR δ 154.40, 154.29, 151.11, 134.77, 119.35, 110.05, 109.76, 108.31, 105.67, 76.65, 49.13, 44.89, 41.36, 36.05, 31.54, 29.48, 29.45, 28.16, 28.05, 27.94, 27.90, 27.87, 27.63, 25.15, 24.93, 23.50, 22.95, 18.52; HRMS (FAB), m/z, calculated for $C_{26}H_{38}O_2$, 382.2872, experimental 382.2878.

Example 2

Receptor Binding Assays

Cell membranes from HEK293 cells transfected with the human CB1 cannabinoid receptor and membranes from CHO-K1 cells transfected with the human CB2 cannabinoid receptor were used in the receptor binding assays. Displacement of [$^3$H]CP 55,940 from the CB1 and CB2 receptor preparations by increasing concentrations of the Δ$^8$-THC analogs 23–29 and Δ$^8$-THC were used to determine the binding affinities of the conformationally biased probes (see Table 1 below). The $K_i$ values for Δ$^8$-THC at the hCB1 and hCB2 receptor were 28.5 nM and 25.0 nM, respectively (affinity ratio CB1/CB2=1.14), compared to a reported value of 47.6 nM for the rCB1 and 39.3 for-the mCB2 (affinity ratio CB1/CB2=1.21)(Busch-Ptersen, J. et al., *J. Med. Chem.* 39:3790 (1996), which is hereby incorporated by reference in its entirety). The LBP probes exhibited a 3 to 143 fold enhancement in binding affinity to the receptor subtypes relative to Δ$^8$-THC. The gem-dimethyl analogs 27–29 and the pentyl dithiolane 23 possessed sub-nanomolar affinities for both the CB1 and CB2 receptors that are comparable to the highly potent 1',1'-dimethylheptyl-Δ$^8$-THC (DMHT, $K_i$=0.77 nM)(Martin, B. R. et al., *Pharmacol. Biochem. Behav.* 43:295 (1993), which is hereby incorporated by reference in its entirety). Within this group of compounds the 1',1'-dimethylcyclopentyl, 27, had the highest affinity for the CB1 receptor ($K_i$=0.34 nM) while the 1',1'-dimethylcycloheptyl, 29, exhibited greater affinity for the CB2 receptor ($K_i$=0.22 nM). Despite the relatively high affinity, only compound 29 demonstrated reasonable selectivity between receptor subtypes. None of the compounds showed significant selectivity (e.g., greater than 10:1) between receptor subtypes.

TABLE 1

Binding affinities of $^8$Δ-THC and analogs 23–29 for the CB1 and CB2 receptors

| Compound | $CB_1$ $K_i$ (nM)$^a$ | $CB_2$ $K_i$ (nM)$^a$ | Ratio $CB_1/CB_2$ |
|---|---|---|---|
| $^8$Δ-THC | 28.5(±3.3) | 25.0(±4.8) | 1.14 |
| 23 | 0.85(±0.02) | 0.58(±0.03) | 1.47 |
| 24 | 9.49(±2.42) | 2.74(±1.10) | 3.46 |
| 25 | 1.86(±0.71) | 1.05(±0.41) | 1.77 |
| 26 | 1.76(±0.56) | 6.62(±0.92) | 0.27 |
| 27 | 0.34(±0.04) | 0.39(±0.06) | 0.84 |
| 28 | 0.57(±0.05) | 0.65(±0.04) | 0.87 |
| 29 | 0.94(±0.05) | 0.22(±0.01) | 4.65 |

$^a$The $K_i$ values for $^8$Δ-THC and the analogs were obtained from n ≥ 2 independent experiments run in triplicate showing the standard error of the mean in parentheses.

The substitution of the 1',1'-dimethyl for the 1',1'-dithiolane group unexpectedly resulted in decreased affinity for both the CB1 and CB2 receptors. This series did not parallel the affinities observed within the synthesized 1',1,-dimethyl analogs and had distinctly higher $K_i$'s than 1',1'-dithiolane-heptyl-Δ$^8$-THC (DTHT, $K_i$=0.32 nM) (Papahatjis, D. P. et al., *J. Med. Chem.* 41:1195 (1998), which is hereby incorporated by reference in its entirety). Within this series of compounds the carbon equivalent of the later, 25, had a $K_i$ of 1.86 nM suggesting the structural requirements of the receptors are related to steric constraints. The 1',1'-dithiolanepentyl analog 23 had a 4.7 fold and 11 fold increased affinity for the CB1 and CB2 receptors, respectively, relative to the carbon equivalent 24. These data combined with the 2 to 28 fold decrease in affinity of 24–26, relative to 27–29, for the CB1 suggest that this series may help define the steric limitations of the LBP. Furthermore, based on the steric requirements of the dithiolane series, modest receptor subtype selectivity is observed when considering the 1.76 nM $K_i$ of 26 for the CB1 receptor and the 2.74 nM $K_i$ of 24 for the CB2 receptor. The overall results of the receptor binding studies on both series suggest that these Δ⁸-THC analogs will aid in the development of the SAR of the LBP with respect to the CCBs.

Example 3

NMR and Molecular Modeling Studies

The binding affinities of the dimethyl-cycloalkyl analogs for both the CB1 and CB2 receptors are comparable to that of the highly potent 1',1'-dimethylheptyl THC (DMHT, $K_i$=0.77nM) analog. Molecular modeling analysis of these compounds shows that the linear dimension of DMHT is 7.72 Å compared to 4.55 Å for 28, which is the cyclic carbon equivalent of DMHT. The difference of 3.17 Å in the linear length of the side chain suggested that there is a region in the LBP that accommodates the C3 substituent which can be characterized as a hydrophobic ellipsoid. It remains unclear if this is the same pocket that accommodates the side chain of linear analogs; however, the potential existence of an ellipsoid pocket made it important to characterize the relative geometry of the cyclic side chain with respect to the tricyclic ring system. One facet of this effort utilized 1D and 2D high field NMR spectroscopy to assess the relative side chain geometries; furthermore, extensive NOESY studies on 28 were conducted to obtain distance constraints for use in molecular modeling.

The chemical shifts of the constituent protons in analogs 23–29 were first assigned utilizing 1D, gHSQC, gHMBC, and gCOSY experiments. Based on these assignments the relative spatial orientations of the protons were examined via 2D NOESY experiments. In all the derivatives a network of NOEs interconnecting the tricyclic ring system protons were observed. The NOESY experiments on 27–29 show strong NOEs between the H2 and H4 protons of the aromatic ring and the dimethyl and cycloalkyl methyne protons (FIG. 1); furthermore, the methylene units alpha to the methyne of the cycloalkyls show medium NOEs to the aromatic protons. A similar pattern is observed with respect to the dithiolane probes 24–26 with the notable addition of two weak NOEs to one each of the dithiolane methylenes. The presence of these NOEs to the dithiolane methylene and the multiplet between 3.07–3.33 ppm, i.e. diastereotopic protons (FIG. 2), observed for these protons suggests that the ring flexibility is restrained and as such the protons reside in unique regions of the aromatic shielding/desheilding cone. The NOE patterns and intensities observed for the LBP probes suggest a conformational bias of the C3 side chains.

Figure 2:
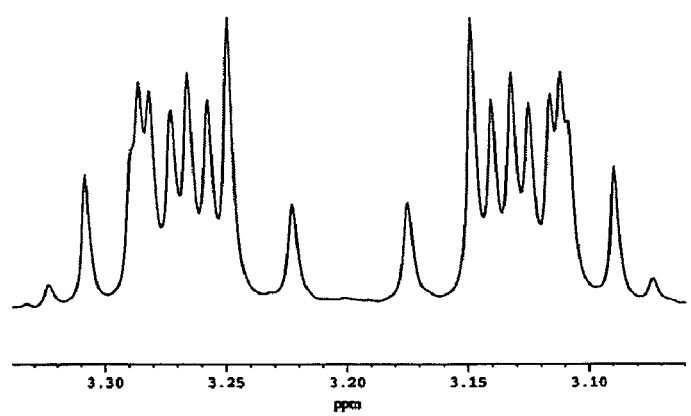
FIG. 2 is a partial 1D NMR spectra of compound 25 showing the diastereotopic methylene protons of the dithiolane group.
Figure 3:
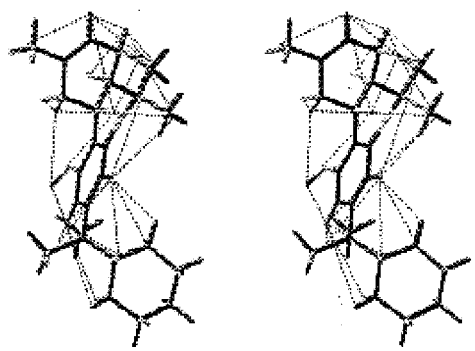
FIG. 3 is a stereoscopic view of compound 28 showing the NOE constraints (dashed yellow lines) derived from the 2D NOESY experiments. Carbon atoms are shown in white, hydrogen atoms in cyan and oxygen atoms are red.
Figure 4:
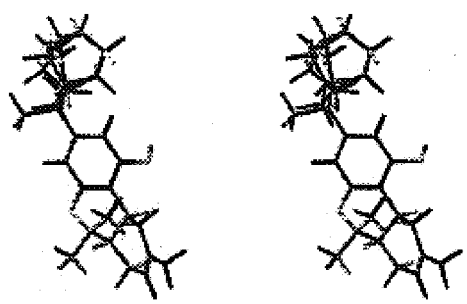
FIG. 4 is a stereoscopic views of compound 28 showing the two cyclohexyl side-chain conformations identified in the molecular dynamics studies. Carbon atoms are shown in white, hydrogen atoms in cyan and oxygen atoms are red.

A qualitative analysis of the NOE intensities combined with model building suggest that cycloalkyl functionalities extend away from the aromatic ring and do not fold over the ring in solution, i.e. the distinct absence of NOEs between the H4'–H6' and H2/H4 protons (FIG. 1). To more accurately examine the relative ring orientation, NOESY experiments using mixing times from 300–700 ms over 100 ms intervals were carried out on 28. This analog was selected for investigation because it is the carbon equivalent of DMHT. The spectra exhibited 41 clearly resolved NOEs with a subpopulation of 8 signals arising from the cyclohexyl to the H2 and H4 protons. Integration of those non-overlapping unambiguously assigned peaks utilizing TRIPOS TRIAD software followed by constraint generation using MARDIGRAS resulted in a web of 26 distance constraints (FIG. 3)(SYBYL, version 6.8, Tripos, Inc.: St. Louis, Mo. (2001), which is hereby incorporated by reference in its entirety). Utilizing these constraints, the model was subjected to 1 ns of constrained molecular dynamics to determine the populations of torsional conformers associated with the experimental NMR data. The resulting conformations show a single constraint violation between the cyclohexane methyne and one of the aromatic protons, most likely due to interconversion between the 41 and 319 degree torsional angles for the C3—C1'—C2'—C3' ($\tau_2$) bond, representing the two torsional populations observed in the simulated annealing studies (FIG. 4). Multiple torsional driving utilizing grid searches failed to predict these geometries suggesting that electronic effects were responsible for the conformations observed in the NMR studies. Therefore, quantum mechanical calculations were employed to examine the electronic effects driving the structural bias.

Example 4

Quantum Mechanical Calculations

It seemed reasonable to assume that the gem-dimethyl would adopt a conformer that would maximize the interaction between the conformationally biased side chain and the aromatic ring. However, the conformation of the cyclohexyl analog 28 predicted by NMR and molecular dynamics could not be explained based on molecular mechanics calculations, i.e. electrostatic and steric analysis. To address this issue, semi-empirical and density functional theory (DFT) calculations have been employed to critically evaluate the potential conformers and determine the importance of electronic contributions in the experimental results.

Figure 5:
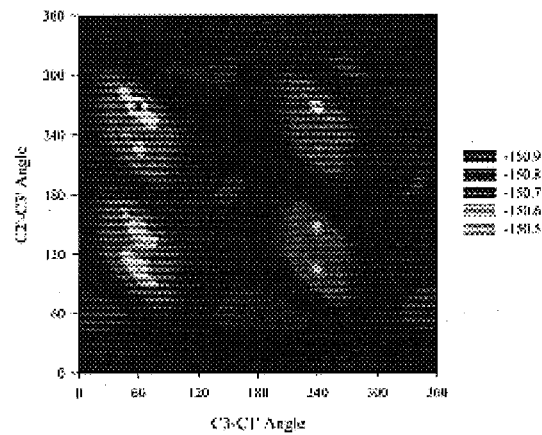
FIG. 5 is a calculated PM3 potential energy surface of compound 28 as a function of torsional parameters $\theta_{\tau 1}$ and $\phi_{\tau 2}$. Reported energies are the calculated heat of formation in Hartrees. The AM1 potential energy surface has identical qualitative features.

Geometry optimizations were performed using both the AM1 and PM3 semi-empirical parameterizations with the GAMESS computational chemistry package (Schmidt, M. W. et al., *J. Comput. Chem*. 14:1347 (1993), which is hereby incorporated by reference in its entirety). The stationary points were confirmed by calculating the Hessian at the optimized geometries. Using these optimized structures, the potential energy surface (PES) was calculated using both AM1 and PM3 as a function of the rotations around the C2—C3—C1'—C2' ($\tau_1$) and C3—C1'—C2'—C3' ($\tau_2$) bonds with all other geometric parameters held constant. Both semi-empirical potential energy surfaces show that there is relatively free rotation about the $\tau_1$ and $\tau_2$ bonds (FIG. 5). More pronounced "ridges" on the PM3 surface result from more diffuse electron densities produced with the PM3 parameterization relative to AM1. The four large peaks in the PES are the result of near collisions between a methylene hydrogen on the cyclohexyl group and the C2 hydrogen of the THC moiety. The most severe of these collisions arise from a 1.03 Å separation between two hydrogen atoms.

There are six regions on the PES that represent local minima for analog 28 which can be designated by ordered pairs of angles according to ($\theta_{\tau_1}$, $\phi_{\tau_2}$) as A(141,56), B(259, 301), C(270,180), D(323,56), E(40,305), and F(108,190). Geometry optimizations at the PM3 level were performed to identify the local minima nearest to each of these points followed by a DFT energy calculation using the B3LYP functional and a 6-31G(p,d) basis set. In addition, the associated conformer obtained by an 180° rotation about the $\tau_1$ bond was identified in the same manner (designated A', B', etc.). The range of values for the $\tau_2$ dihedral is 56 to 305 degrees for the quantum mechanical calculations whereas the dynamics study predicted a range of 41 to 319. The relative energies for the six lowest energy conformations at the B3LYP/6-31G(p,) level (Hehre, W. J. et al., *J. Chem. Phys*. 2257:56 (1972); Hariharan, P. C. et al., *Theoret. Chimica Acta* 28:213 (1973), which are hereby incorporated by reference in their entirety), are given in Table 2 below. Note that the largest energy difference between these structures is only 0.6 kcal/mol (roughly 8.8 milliHartrees) suggesting that all conformers are thermally accessible. Observed deviations between the molecular modeling results and the quantum mechanical results are small enough, i.e. within 10%, to justify agreement between the two methods.

TABLE 2

Relative energy differences (kcal/mol) between the six lowest energies on the potential energy surface for the gem-dimethyl analog (Huffman et al., J. Med Chem. 39: 3875 (1996)).

| Conformation[a] | ΔE (kcal/mol) |
|---|---|
| F' (101,60) | 0.55 |
| B (259,301) | 0.52 |
| A (141,56) | 0.38 |
| A' (124,193) | 0.09 |
| F (108,190) | 0.05 |
| D' (302,193) | 0.00 |

[a]Numbers in parenthesis are the ordered pairs of angles ($\theta_{\tau 1}$, $\theta_{\tau 2}$)

However, the NMR data suggests that there is a preferred conformation in the solvent phase, suggesting that the electronic contributions may be important. FIG. 6B shows the HOMO orbital diagram (from the B3LYP/6-31G(p,d) calculations) for the gem-dimethyl analog 28. In this conformation there is an orbital lobe associated with the hydrogen atom bonded to the C3' carbon atom. The shape of this lobe suggests an anti-bonding sigmna orbital and indicates a repulsive interaction between the hydrogen atom and the electron density of the aromatic ring. An examination of the shape of the orbital lobes associated with the aromatic ring shows a deformation associated with this hydrogen interaction. FIG. 6A shows the HOMO orbital diagram for the same compound after a rotation of 180 degrees about the $\tau_2$ angle and a subsequent reoptimization as described previously. In this case we notice two such repulsions between the aromatic ring and the nearest hydrogen atom causing an increase in energy of 0.28 kcal/mol. Although small, this energy could be sufficient to cause conformational preference in the solvent phase. This feature can be observed because of the quality of the B3LYP functional and the presence of diffuse functions in the 6-31G(p,d) basis set. By comparison with the experimental results we can surmise that the bias in the NMR spectrum is the result of electronic interactions between the aromatic ring and the terminal hydrogens of the cyclohexyl group, favoring conformations that minimize the number of such repulsions.

Discussion of Examples 1–4

The design and synthesis of the novel $\Delta^8$-THC analogs allowed for probing of the side chain LBP pocket of the CB1 and CB2 receptors. It was hypothesized that cycloalkyl side chains that contain identical carbon numbers as known high affinity ligands but that have reduced linear dimensions may provide insight into the side chain pocket geometry. To this end seven novel $\Delta^8$-THC analogs were synthesized and tested for binding affinity to the human CB1 and CB2 receptors. The dimethylcycloalkyl analogs 27–29 had $K_i$ values (0.34 to 0.94 nM) comparable to those of highly potent CB1 analogs such as DHMT (0.77 nM), the 1',2'-dimethylheptyls (0.46–0.84 nM). In contrast, the introduction of the 1',1'-dithiolane ring to the cycloalkyl analogs decreased receptor binding as compared to the dimethyl series. The notable exception is 23 wherein a 33 and 47 fold increase in binding to the CB1 and CB2 receptors, respectively, is observed relative to $\Delta^8$-THC. Caution must also be exercised when comparing receptor binding data from different species and that obtained from different receptor preparations; however, the affinity ratio for the hCB1 to rCB1 found in our assays was 1.67 while the ratio for the hCB2 to mCB2 was 1.57. Factoring in this ratio our compounds remain comparable to other known high affinity CB ligands.

The most significant difference in CB1 affinity occurs within the cyclopentyl and pentyl compounds 23, 24, and 27. Interestingly, 23 and 27 have high affinities for the CB1 receptor in contrast to 24 that has an 11 to 28 fold decrease in CB1 affinity. The physical basis for the increased $K_i$ for 24 may reflect the limited rotation of $\tau_1$ due the dithiolane ring that thus prevents the cyclopentyl group from optimizing interactions with the receptor. This limitation to rotation about $\tau_1$ and $\tau_2$ is not predicted based on the NMR and quantum mechanical calculations on 28 thus suggesting that 27 can adopt geometries that maximize receptor interactions. In particular, despite the conformational flexibility about $\tau_2$, the steric bulk of the cyclohexyl group prevents free rotation about $\tau_1$. Analog 23 is not restricted by the steric constraints associated with the cyclic analogs and as such can adopt receptor favorable conformations. In contrast to the affinities of 24–26 for the CB1 receptor the dithiolane ring does not appear to be as well tolerated by the CB2 receptor, i.e. a 7 and 33 fold decrease in affinity for 24 and 26. This combined with the data for CB1 affinity suggests that the LBP side chain requirements between the receptor subtypes are sensitive to steric bulk.

By far the most important finding of this study is that cycloalkyl side chains bind to both the CB1 and CB2 receptors with affinities comparable to the linear chain-$\Delta^8$-THC analogs, e.g. DMHT. An analysis of the maximum linear dimensions for the cyclic side chain analogs range from 3.90 Å for 27 to 4.99 Å for 29 compared to 7.72 Å for DMHT. These distances combined with the receptor binding data suggest the existence of an ellipsoidal hydrophobic pocket that may or may not represent the pocket occupied by the linear side chain analogs. The orientation of the C3 side chain in solution with respect to the tricyclic ring system projects 124 degrees from the plane of the aromatic ring base on NMR and quantum mechanical calculations. The results of these studies provide insights into the solution conformations of the $\Delta^8$-THC analogs, which may reflect the LBP spatial constraints of these CB ligands. The orientation of the side C3 side chain in the LBP cannot be conclusively defined since ligands do bind receptors in conformations different from solution or crystal structures. Furthermore, the analog affinities cannot be correlated with ligand efficacy since a number of high affinity ligands exhibit poor efficacy in functional assays (Griffin, G. et al., Br. J. Pharmacol. 132:525–35 (2001), which is hereby incorporated by reference in its entirety). Functional assays on this series of compounds will ultimately permit us to refine the structural requirements of the LBD of the CB receptors and properties of these analogs.

Analogs 27–29 have affinities for the CB1 and CB2 receptors comparable to known high affinity CCB ligands while the dithiolane derivatives 24 and 26 have reduced affinity. The receptor binding data suggest that the side chain binding pocket for this series of compounds can be characterized as a hydrophobic ellipsoid. Though the functional potency need not correlate with binding affinities, the $K_i$ values give an indication of part of the receptor structure and provide for improvement on the CCB structure to produce higher affinity analogs. The determination of the functional activity of the reported compounds combined with SAR studies on the CCBs should provide invaluable insights into the development of this class of CB receptor analogs. Furthermore, the aforementioned studies may help clarify if the ellipsoid pocket is the same pocket occupied by the linear side chain CB analogs.

Example 5

Synthesis of $\Delta^8$-THC Analogs Containing 1'-Phenyl Functionality

The side chains of classical cannabinoids have often been made by reaction of 3,5-dimethoxy benzonitrile with a suitable Grignard reagent and acid hydrolysis of the intermediate imine salt to the ketone (Singer et al., *J. Med. Chem.* 41:4400 (1998), which is hereby incorporated by reference in its entirety). Due to the reduced reactivity of aromatic Grignard reagent as compared to alkyl Grignard reagent, 3,5-dimethoxy benzaldehyde was selected as the starting material and reacted this with phenyl magnesium bromide to obtain the corresponding alcohol (37) (Frenette et al., *J. Org. Chem.* 56:3083 (1991), which is hereby incorporated by reference in its entirety) as shown in FIGS. 8A–B. Oxidation of alcohol with PCC yielded the key intermediate ketone (38) (Frenette et al., *J. Org. Chem.* 56:3083 (1991), which is hereby incorporated by reference in its entirety). The dithiolane group was introduced at the C1' position (40) by reacting the ketone with ethane dithiol in presence of boron trifluoride (Papahatjis et al., *J. Med. Chem.* 41:1195 (1998), which is hereby incorporated by reference in its entirety). The ketone intermediate was also reacted with dimethyl zinc and titanium tetrachloride to form the dimethyl substituent at the C1' position (39) (Singer et al., *J. Med. Chem.* 41:4400 (1998), which is hereby incorporated by reference in its entirety). Desulfurisation of intermediate (40) with Raney Nickel yielded the methylene intermediate (41) (Sondheimer et al., *Tetrahedron. Lett.*, 80:3995 (1958), which is hereby incorporated by reference in its entirety). The 1-substituted 3,5-dimethoxy intermediates (39–41) were deprotected with boron tribromide to yield the corresponding resorcinols (42–44) (Singer et al., *J. Med. Chem.* 41:4400 (1998), which is hereby incorporated by reference in its entirety). $\Delta^8$-THC analogs (33–35) were then obtained from these resorcinols (42–44) by reacting them with cis-$\Delta^2$-p-menthene-1,8-diol, prepared from (+)-$\Delta^2$-carene, (Prasad et al., *Tetrahedron* 32:1437 (1976), which is hereby incorporated by reference in its entirety) in presence of p-toluene sulfonic acid. The $\Delta^8$-THC analog with a ketone functionality at the C1' position (37) was obtained by deprotecting the analog (34) with silver nitrate (Reece et al., *Tetrahedron*, 24:4249 (1968), which is incorporated by reference in its entirety).

Compound 33: gem-dimethyl-phenyl-$\Delta^8$-THC $R_f$=0.42 (methylene chloride:hexane 50:50), $R_f$=0.6 (ethyl acetate:petroleum ether 10:90), $^1$H NMR (CDCl$_3$) δ 7.14 ppm (m, 5H), 6.36 ppm (d, J=1.8 Hz, 1H), 5.91 ppm (d, J=2.1 Hz, 1H), 5.35 ppm (d, J=6 Hz, 1H), 4.44 ppm (s, 1H), 3.1 ppm (m, 1H), 2.61 ppm (m, 1H), 2.05 ppm (m, 1H), 1.75 ppm (m, 3H), 1.62 ppm (s, 3H), 1.54 ppm (m, 6H), 1.31 ppm (s, 3H), 1.04 ppm (s, 3H); MS: (ESI, Neg), m/z 361 ([M−1]$^-$). HRMS (FAB), m/z calcd for C$_{25}$H$_{30}$O$_2$, 362.2246, experimental 362.2239.

Compound 34: dithiolanyl-phenyl-$\Delta^8$-THC $R_f$=0.22 (methylene chloride:hexane 50:50), $R_f$=0.58 (ethyl acetate:petroleum ether 20:80), $^1$H NMR (CDCl$_3$) δ 7.54 ppm (m, 2H), 7.18 ppm (m, 3H), 6.65 ppm (d, J=2.1 Hz, 1H), 6.39 ppm (d, J=2.1 Hz, 1H), 5.35 ppm (d, J=4.2 Hz, 1H), 4.61 ppm (s, 1H), 3.32 ppm (m, 4H), 3.1 ppm (m, 1H), 2.62 ppm (m, 1H), 2.06 ppm (m, 1H), 1.76 ppm (m, 3H), 1.62 ppm (s, 3H), 1.29 ppm (s, 3H), 1.03 ppm (s, 3H); MS: (ESI, Neg), m/z 423 ([M−1]$^-$). HRMS (FAB), m/z calcd for C$_{25}$H$_{28}$O$_2$S$_2$, 424.1531, experimental 424.1533.

Compound 35: methylene-phenyl-$\Delta^8$-THC $R_f$=0.34 (methylene chloride:hexane 50:50), $R_f$=0.42 (ethyl acetate:petroleum ether 10:90), $^1$H NMR (CDCl$_3$) δ 7.22 ppm (m, 3H), 7.13 ppm (m, 2H), 6.22 ppm (m, 1H), 5.98 ppm (m, 1H), 5.35 ppm (d, J=6 Hz, 1H), 4.52 ppm (s, 1H), 3.74 ppm (s, 2H), 3.1 ppm (m, 1H), 2.62 ppm (m, 1H), 2.07 ppm (m, 1H), 1.75 ppm (m, 3H), 1.62 ppm (s, 3H), 1.29 ppm (s, 3H), 1.03 ppm (s, 3H); MS: (ESI, Neg), m/z 333 ([M−1]$^-$). HRMS (FAB), m/z calcd for C$_{23}$H$_{26}$O$_2$, 334.1933, experimental 334.1928.

Compound 36: methanone-phenyl-$\Delta^8$-THC $R_f$=0.2 (methylene chloride:hexane 60:40), $R_f$=0.47 (ethyl acetate:petroleum ether 20:80), $^1$H NMR (CDCl$_3$) δ 7.82 ppm (m, 2H), 7.58 ppm (m, 1H), 7.48 ppm (m, 2H), 6.92 ppm (d, J=1.8 Hz, 1H), 6.83 ppm (d, J=1.5 Hz, 1H), 5.48 ppm (m, 2H), 3.34 ppm (m, 1H), 2.81 ppm (m, 1H), 2.18 ppm (m, 1H), 1.88 ppm (m, 3H), 1.74 ppm (s, 3H), 1.41 ppm (s, 3H), 1.12 ppm (s, 3H); MS: (ESI, Neg), m/z 347 ([M−1]$^-$). HRMS (FAB), m/z calcd for C$_{23}$H$_{24}$O$_3$, 348.1725, experimental 348.1717.

The CB1 and CB2 binding affinities of these novel $\Delta^8$-THC analogs with phenyl side chains were determined using membrane preparations of the human receptors transfected into HEK293 EBNA cells. Receptor binding assays were carried out using tritiated CP55,940 as the competing radioactive ligand and 10 μm WIN 55212–2 was used for determining non-specific binding (Nadipurarn et al., *Bioorg. Med. Chem.* 11:3121 (2003), which is hereby incorporated by reference in its entirety).

The CB2 binding affinities of these novel analogs were in the range of 0.9–86 nm while the CB1 binding affinities ranged from 12–297 nM (Table 3 below). Interestingly, these compounds exhibited significantly different binding profile when compared to the lead compound (32). The dimethyl analog (33) exhibited good binding affinities for both the CB1 and the CB2 receptors with a 13-fold selectivity for the CB2 receptor. This selectivity is in contrast to the lead compound (32) that binds both the subtypes with almost equal affinity. The ketone analog (36) exhibited similar binding affinity for the CB2 receptor when compared to $\Delta^8$-THC but almost a 10-fold decrease in the binding affinity for the CB1 receptor. The dithiolane analog (34) exhibited no subtype selectivity, however there was a 10 fold decrease in affinity relative to the 1'-cyclohexyl congener (CB1 K$_i$=1.86 nM and CB2 K$_i$=1.05 nM) (Nadipuram et al., *Bioorg. Med. Chem.* 11:3121 (2003), which is hereby incorporated by reference in its entirety). The methylene analog (5) displayed significantly reduced binding affinities for both the subtypes in comparison to $\Delta^8$-THC.

TABLE 3

Affinities ($K_i$) of compounds 33–36 for CB1 and CB2 receptors

| Compound | CB1 $K_i$ (nM)[a] | CB2 $K_i$ (nM)[a] | Ratio CB1/CB2 |
|---|---|---|---|
| $\Delta^8$-THC | 28.5 (±3.30) | 25.0 (±4.80) | 1.14 |
| 28 | 0.57 (±0.05) | 0.65 (±0.04) | 0.87 |
| 33 | 12.3 (±0.61) | 0.91 (±0.08) | 13.5 |
| 34 | 17.3 (±0.33) | 17.6 (±1.03) | 0.98 |
| 35 | 67.6 (±2.90) | 85.9 (±0.31) | 0.78 |
| 36 | 297 (±10.6) | 23.6 (±1.76) | 12.6 |

[a]The $K_i$ values for $\Delta^8$-THC and the analogs were obtained from three independent experiments each of which was run in duplicate and are expressed as the mean of three values, with the standard error of mean shown in parentheses.

The binding affinities of the 1'-phenyl substituted $\Delta^8$-THC analogs provide some new insights into the functional group requirements of the binding pockets of the CB1 and CB2 receptors. Valuable structural information can be gleaned from our dimethyl and ketone analogs that exhibited modest selectivity for the CB2 receptor. This in combination with our previous data for the cyclohexyl $\Delta^8$-THC analogs (Nadipuram et al., Bioorg. Med. Chem. 11:3121(2003), which is hereby incorporated by reference in its entirety) suggests that a subsite binding pocket of the CB2 receptor can tolerate both cycloalkyl side chains and rigid aromatic side chains when compared to the CB1 receptor. The selectivity of 33 and 36 is interesting when considering that several of the short chain C3 analogs reported by Huffman et al. also exhibited significant CB2 selectivity (Huffman et al., Bioorg. Med. Chem. 10:4119 (2002), which is hereby incorporated by reference in its entirety). A comparison between the two structural types is difficult when considering that the short chain analogs were primarily 1-deoxy and 1-methoxy compounds as compared to our 1-hydroxy analogs. Notwithstanding, the modest selectivity of our 1-hydroxy compounds might suggest the presence of favorable interactions between the phenyl side chain and aromatic amino acids that may be present in the binding pocket of the CB2 receptor. Although it is difficult to draw any direct comparisons, aromatic residues have been proposed to reside in the LBP of the CB1 receptor (Papahatjis et al., J. Med. Chem. 41:1195 (1998), which is hereby incorporated by referenced in its entirety). In contrast, reduced CB1 binding affinities exhibited by these compounds relative to the cyclohexyl (Nadipuram et al., Bioorg. Med. Chem. 11:3121(2003), which is hereby incorporated by reference in its entirety) and linear chain derivatives (Papahatjis et al., J. Med. Chem. 41:1195 (1998), which is hereby incorporated by reference in its entirety) may suggest that the compounds cannot adopt a conformation to maximize ligand-receptor interactions. The presence of a the polar C1' keto group may also diminish CB1 affinity as has been previously proposed by Papahatjis and coworkers (Papahatjis et al., J. Med. Chem. 41:1195 (1998), which is hereby incorporated by reference in its entirety). Further studies utilizing substituted C1' phenyl groups should provide additional insight into the SAR of this class of $\Delta^8$-THC analogs. Combining these studies with functional assays should contribute to a better understanding about the differences in the structural requirements of the LBP of the CB1 and CB2 receptors and may aid in developing more selective compounds.

Examples 6

Analysis of the NMR and Electronic Structures of 1'-phenyl $\Delta^8$-THC Analogs All calculations were performed with the GAMESS (Schmidt, M. W. et al., J. Comput. Chem., 14:1347 (1993), which is hereby incorporated by reference in its entirety) computational chemistry package on a Silicon Graphics Origin 2000 with 8 processors and 4GB total memory. Initial geometry optimizations were performed using the PM3 semi-empirical Hamiltonian with a subsequent numerical Hessian to verify that each structure was a local minimum. The resulting structures were then taken as a reference point for the calculation of the potential energy surface.

Two dihedral angles were chosen to represent torsions around the C3—C1' bond and rotations of the front-side phenyl group about its bond to C1'. We shall henceforth refer to these two angles as $\tau_1$ and $\tau_2$, respectively. The potential energy surface (PES) calculations were performed at the PM3 level of theory in ten-degree increments about each of the torsion angles from 0 to 360 degrees. All other geometric parameters were held fixed at the values obtained from the initial PM3 geometry optimization. The optimized structures are available as supplemental information in the form of PDB (protein data bank) files. The two torsion angles are defined according to the set of four atoms in the corresponding PDB files as follows: compound 34 (dithiolanyl-phenyl-$\Delta^8$-THC) ($\tau_1$: 6,1,19,40 $\tau_2$: 40,19,41,49); compound 33 (gem-dimethyl-phenyl-$\Delta^8$-THC) ($\tau_1$: 2,1,19,20 $\tau_2$: 20,19,41,42); compound 35 (methylene-phenyl-$\Delta^8$-THC) ($\tau_1$: 2,1,19, 20 $\tau_2$: 20,19,41,42); compound 36 (methanone-phenyl-$\Delta^8$-THC) ($\tau_1$: 2,1,19,39 $\tau_2$: 39,19,40,41). Resulting energies were normalized with respect to the lowest energy structure and the resulting potential energy surfaces are plotted in FIGS. 10–13 using a logarithmic scale to highlight the salient features. Darker colors represent regions of low energy with lighter colors representing higher energy.

Local minima were identified on each PES and subjected to a geometry optimization with the PM3 Hamiltonian. Structures from this set that could not be confirmed as local minima via a numerical Hessian calculation were discarded in subsequent calculations.

A density functional theory calculation using B3LYP/6-31G(p,d) (Lee et al., Physical Review B, 37:785 (1988); Hehre et al., J. Chem. Phys. 56:2257 (1972); Hariharan et al., Theoret. Chimica Acta, 28:213 (1973), which are hereby incorporated in their entirety) was then performed on each of the identified local minima. Molecular orbital surfaces were generated from the DFT results using a version of MOLDEN (Schaftenaar et al., J. Comput.-Aided Mol. Design, 14:123 (2000), which is hereby incorporated by reference in its entirety), modified at The University of Memphis.

All spectra were acquired at 23° C. and 500 MHz on a Varian Inova-500 spectrometer using a 5-mm HCN triple resonance probe. Both proton and carbon chemical shifts were referenced to the residual solvent peak of $CDCl_3$ (7.24 ppm for proton and 77 ppm for carbon). For two-dimensional NOESY measurements, a total of 1024 fids were recorded for the indirect dimension, with a 2 second recycle delay, with a 500 ms mixing time. The TRIAD NMR package within the Sybyl ("SYBYL, version 6.8", St. Louis, Mo.: Tripos, Inc. 2001, which is hereby incorporated by reference in its entirety) software was used for data processing and analysis. Peaks in the NOESY spectra were assigned and integrated using TRIAD standard functions. MARDI- GRAS was then used to generate distance constraints using these peak integrals. The resulting constraints were then examined to ensure that the error in distances conformed to established errors for NOE constraints wherein; x<2.5 Å was +/−0.1 Å; x≦3.0 Å was +/−0.2Å; x≦3.5 Å was +/−0.3 Å; and x≧3.5 was +/−0.4 Å.

Ten cycles of simulated annealing using the constraints generated by MARDIGRAS were performed on each of the phenyl compounds of Example 5 (e.g., Compounds 33, 34, 35, and 36) by heating to 1000K for 1 ps followed by exponential cooling to 200K then equilibrating for 5 ps. The experimentally obtained NOE distance constraints were applied during all steps of the simulated annealing runs. These averaged conformations of unique rotomers were then minimized with a gradient tolerance of 0.005 kcal·mol$^{-1}$·Å$^{-1}$ without experimental NOE distance constraints to obtain the final average conformations. Additional parameters included the Tripos force field with MMFF94 charges, an 8 Å nonbonding cutoffs, and distance dependent dielectric constant function.

Each of the phenyl derivatives showed a great deal of conformational flexibility resulting in a large number of local minima. Table 4 (below) shows the complete set of minima identified and the relative DFT energies of the structures in kcal/mol as well as the HOMO-LUMO energy gaps for each local minimum. Orbital energies for the lowest energy conformations spanning the HOMO-4 through the LUMO+4 are reported in Table 5 below. Comparing the lowest energy minima with the NMR derived results as shown in Table 6 clearly demonstrates that a true understanding of the most likely conformations for these molecules requires a more sophisticated approach.

TABLE 4

Local minima for each of the cannabinoid derivatives. Individual minima are identified by two torsion angles, $\tau_1$ and $\tau_2$, describing rotations about the C3—C1' and C1'—C2' bonds, respectively.

| Structure | $\tau_1$ | $\tau_2$ | B3LYP/6-31G(p,d) Energy (kcal/mol) | $\epsilon_{LUMO} - \epsilon_{HOMO}$ (eV) |
|---|---|---|---|---|
| 34 | | | | |
| A | 12.5 | 70.2 | 0.3902967256 | 5.0858 |
| B | 195.3 | 54.4 | 0.7096905541 | 5.1648 |
| C | 289.2 | 350.4 | 0.0000000000 | 5.2083 |
| D | 14.4 | 244.0 | 0.5320270930 | 5.0913 |
| E | 195.3 | 232.5 | 0.7028935561 | 5.1648 |
| F | 192.5 | 251.0 | 0.3318524708 | 5.0967 |
| G | 287.8 | 173.6 | 0.1063617186 | 5.1974 |
| 33 | | | | |
| A | 34.3 | 37.7 | 0.0160585407 | 5.4668 |
| B | 149.5 | 30.5 | 1.0874224001 | 5.4777 |
| C | 211.1 | 37.7 | 0.4214233453 | 5.5648 |
| D | 264.7 | 25.0 | 0.4654370082 | 5.5621 |
| E | 329.2 | 32.4 | 0.9355206637 | 5.4750 |
| F | 155.6 | 96.2 | 0.5361974605 | 5.6981 |
| G | 322.9 | 147.4 | 0.4822259701 | 5.6872 |
| H | 35.1 | 216.4 | 0.0000000000 | 5.4668 |
| I | 149.4 | 208.5 | 1.0769039554 | 5.4777 |
| J | 209.3 | 216.9 | 0.4025041130 | 5.5648 |
| K | 265.6 | 203.5 | 0.5046305800 | 5.5621 |
| L | 329.1 | 210.3 | 0.9404394620 | 5.4750 |
| M | 155.5 | 278.8 | 0.5385671885 | 5.6981 |
| 35 | | | | |
| A | 145.0 | 30.0 | 0.0331391691 | 5.5212 |
| B | 167.3 | 10.4 | 1.6556365400 | 5.5348 |
| C | 124.7 | 50.7 | 1.5434561111 | 5.4913 |
| D | 330.4 | 35.0 | 0.0243141223 | 5.5185 |
| E | 349.3 | 12.7 | 1.5045033147 | 5.4913 |

TABLE 4-continued

Local minima for each of the cannabinoid derivatives. Individual minima are identified by two torsion angles, $\tau_1$ and $\tau_2$, describing rotations about the C3—C1' and C1'—C2' bonds, respectively.

| Structure | $\tau_1$ | $\tau_2$ | B3LYP/6-31G(p,d) Energy (kcal/mol) | $\epsilon_{LUMO} - \epsilon_{HOMO}$ (eV) |
|---|---|---|---|---|
| F | 307.4 | 52.0 | 1.5525256358 | 5.5267 |
| G | 309.0 | 53.1 | 1.5753843118 | 5.5348 |
| H | 144.6 | 207.9 | 0.0000000000 | 5.5240 |
| I | 166.8 | 191.1 | 1.6320682132 | 5.5403 |
| J | 328.7 | 214.7 | 0.0015689628 | 5.5185 |
| K | 349.1 | 193.3 | 1.4826145808 | 5.4940 |
| 36 | | | | |
| A | 89.1 | 31.9 | 2.8299991679 | 4.4763 |
| B | 116.2 | 59.9 | 5.3225938465 | 4.6396 |
| C | 116.6 | 60.4 | 5.3436055102 | 4.6423 |
| D | 235.3 | 37.9 | 0.1206474815 | 4.4491 |
| E | 294.1 | 61.7 | 6.0290937016 | 4.6532 |
| F | 123.1 | 141.3 | 0.1218209248 | 4.4600 |
| G | 243.6 | 118.5 | 5.4655987491 | 4.6396 |
| H | 243.9 | 118.8 | 5.4489920159 | 4.6396 |
| I | 271.1 | 146.2 | 2.9099431006 | 4.4763 |
| J | 88.9 | 213.0 | 2.8060891620 | 4.4818 |
| K | 116.4 | 241.3 | 5.3419550338 | 4.6423 |
| L | 116.5 | 241.4 | 5.3433432737 | 4.6423 |
| M | 233.7 | 220.4 | 0.0000000000 | 4.4545 |
| N | 119.2 | 323.4 | 0.4835226564 | 4.4654 |
| O | 235.5 | 219.0 | 0.1521244398 | 4.4491 |
| P | 243.7 | 299.6 | 5.4644005819 | 4.6396 |
| Q | 245.0 | 301.3 | 5.4301953365 | 4.6369 |
| R | 271.3 | 327.1 | 2.9188175952 | 4.4736 |

TABLE 5

Orbital energies in eV for the lowest energy local minima. The gem-dimethyl-cyclohexyl-Δ$^8$-THC and dithiolane-cyclohexyl-Δ$^8$-THC results are included for comparison.

| | Orbital Energies (eV) | | | | | |
|---|---|---|---|---|---|---|
| Orbital | 4 (C) | 2 | 3 (H) | 1 | 5 (H) | 6 (M) |
| LUMO + 4 | 0.9769 | 1.5837 | 1.3062 | 2.0899 | 1.2871 | 1.1647 |
| LUMO + 3 | 0.7211 | 1.2844 | 0.9061 | 1.9565 | 0.8463 | 0.5932 |
| LUMO + 2 | 0.2068 | 0.9388 | 0.6395 | 1.2817 | 0.8163 | 0.0626 |
| LUMO + 1 | 0.0871 | 0.3918 | 0.2422 | 0.8027 | 0.3075 | 0.0354 |
| LUMO | −0.1333 | 0.0952 | 0.1823 | 0.5633 | 0.1605 | −1.1456 |
| HOMO | −5.3416 | −5.3552 | −5.2845 | −5.3199 | −5.3634 | −5.6001 |
| HOMO − 1 | −5.5811 | −5.5621 | −5.5947 | −5.6301 | −5.6083 | −5.8641 |
| HOMO − 2 | −5.7553 | −5.7553 | −5.7362 | −5.7580 | −5.7553 | −5.9893 |
| HOMO − 3 | −5.8832 | −6.0274 | −6.3621 | −7.2764 | −6.2723 | −6.4192 |
| HOMO − 4 | −6.1934 | −6.0845 | −6.5798 | −7.3090 | −6.4736 | −6.7920 |

TABLE 6

Comparison of the structural parameters for the theoretical and NMR observed structures.

| | PM3 | | NMR | |
|---|---|---|---|---|
| Compound | $\tau_1$ | $\tau_2$ | $\tau_1$ | $\tau_2$ |
| 34 | 289.2 | 350.4 | 325.1 | 340.1 |
| 33 | 35.1 | 216.4 | 312.3 | 262.4 |
| 35 | 144.6 | 207.9 | 229.5 | 161.8 |
| 36 | 233.7 | 220.4 | 277.4 | 277.1 |

Figure 9:
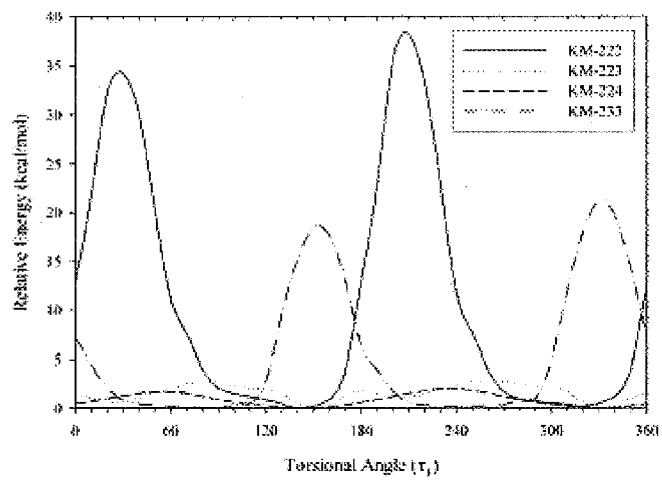
FIG. 9 illustrates the energy versus rotation about the C3—C1' bond for each of the phenyl derivatives. The curves were obtained by fixing the geometry of the front-side of the lowest energy structure and thus represent vertical cross-sections of the potential energy surface. The curves suggest a great deal of conformational flexibility despite some rather large rotational barriers for compound 34 and compound 36. As used in the legend, KM-222 refers to compound 34, KM-222 refers to compound 33, KM-224 refers to compound 35, and KM-233 refers to compound 36.
Figure 10:
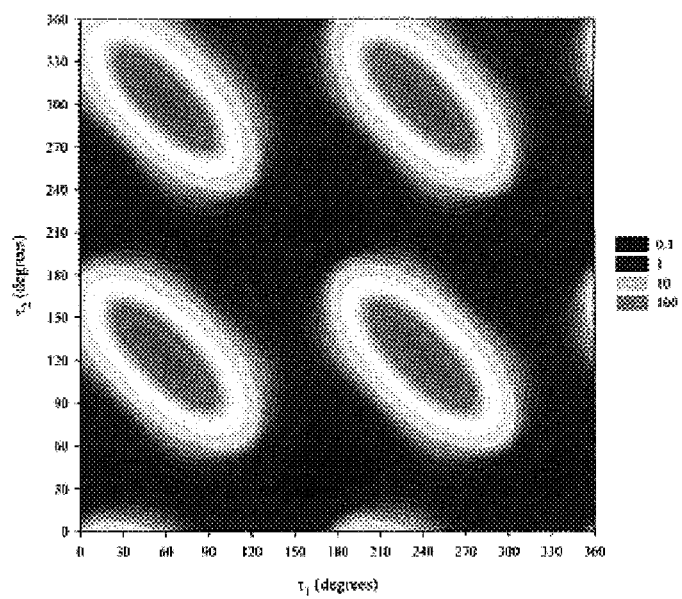
FIG. 10 illustrates calculated PM3 potential energy surface for compound 34. Note the large shallow wells in the surface, e.g. the well near (170,50), indicating a great deal of conformational freedom.
Figure 11:
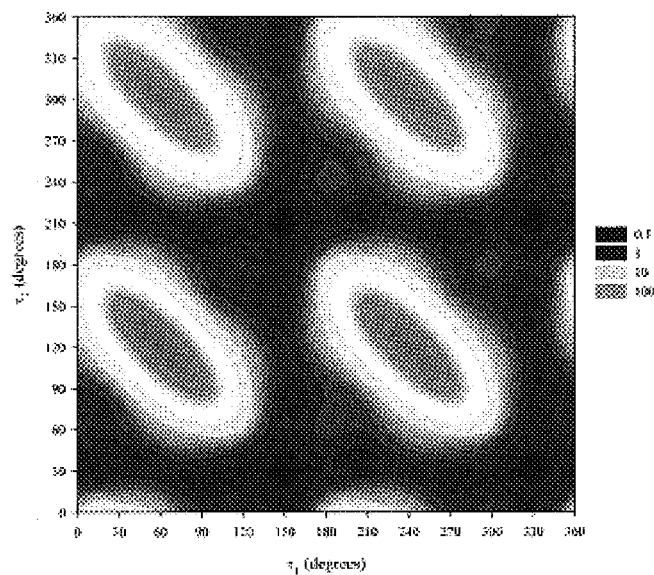
FIG. 11 illustrates calculated PM3 potential energy surface for compound 33. Note the large number of narrow yet shallow wells in this surface, indicating a great number of local minima. Thirteen local minima (see Table 4) were identified for this surface via PM3 calculations.
Figure 12:
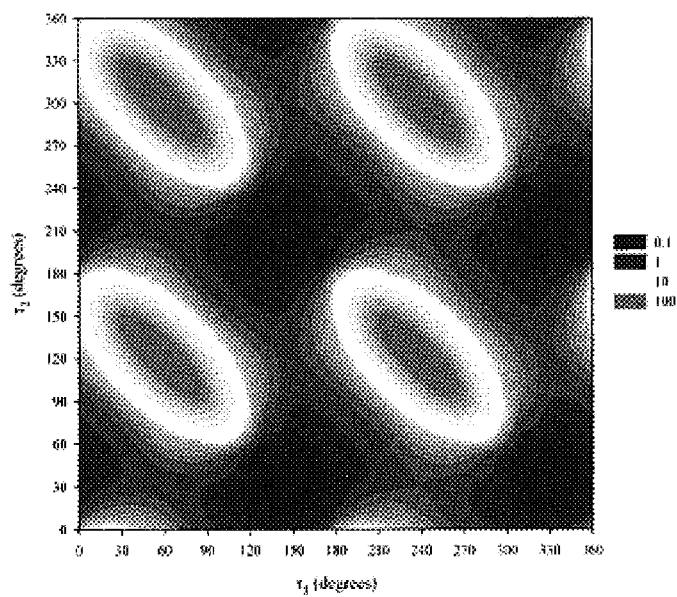
FIG. 12 illustrates calculated PM3 potential energy surface for compound 35. Note the great deal of symmetry present in each well and the similarities between separate wells in this surface. As was the case with the compound 34 potential energy surface, the wells on this surface are quite wide.
Figure 13:
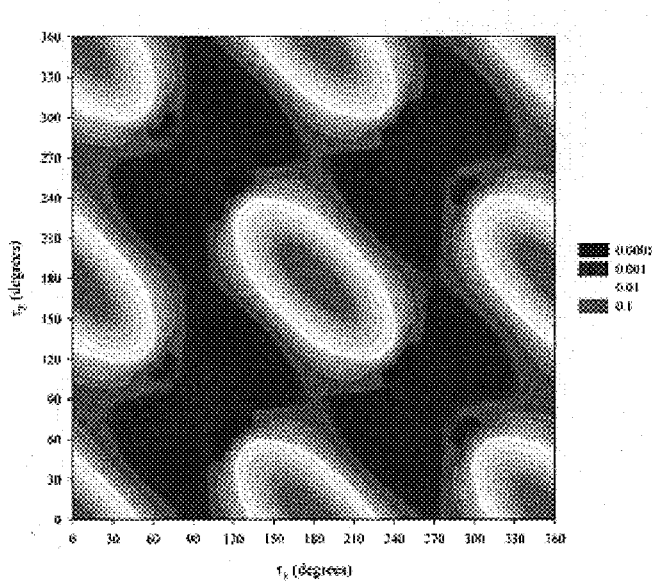
FIG. 13 illustrates calculated PM3 potential energy surface for compound 36. Note the large number of narrow yet deep wells in this surface that result from the strong π interactions between the carbonyl oxygen at the C1' position with the π system from Ring A. Sixteen local minima (see Table 4) were identified for this surface via PM3 calculations.

Given the number of potential local minima for each derivative, we first determined if the entire potential energy surface was accessible for these molecules. To address this question in a first approximation, we plotted the rotational energy barriers for each molecule by taking the lowest-energy structure on the potential energy surface and rotating the front side of the molecule about $\tau_1$ (FIG. 9). Compound 34 (the dithiolane derivative) and compound 36 (the methanone derivative) have significant rotational energy barriers whereas compound 33 (the gem-dimethyl derivative) and compound 35 (the methylene derivative) have rotational energy barriers of less that 3 kcal/mol each. This suggests that compound 33 and compound 35 have access to the entire potential energy surface whereas compound 34 and compound 36 will be confined to particular wells on the potential energy surface.

Figure 14:
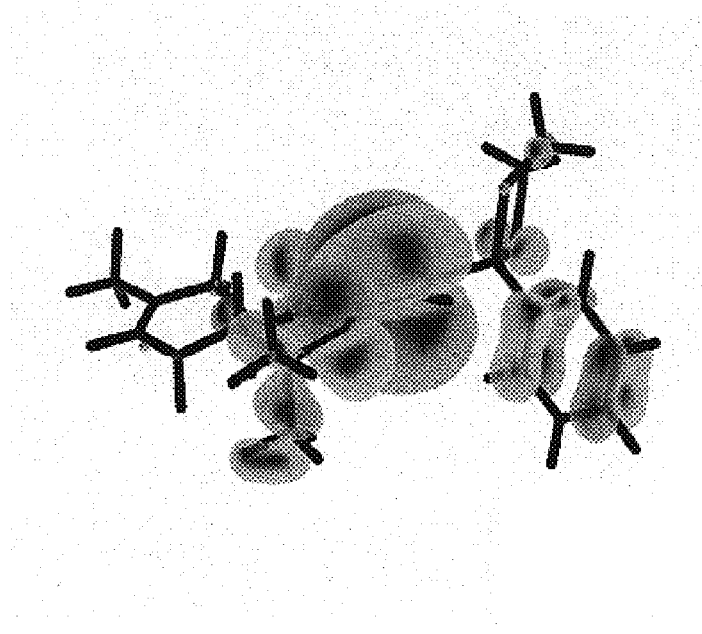
FIG. 14 illustrates a HOMO orbital diagram for the lowest energy conformer of compound 34 (C) as defined in Table 4.
Figure 15:
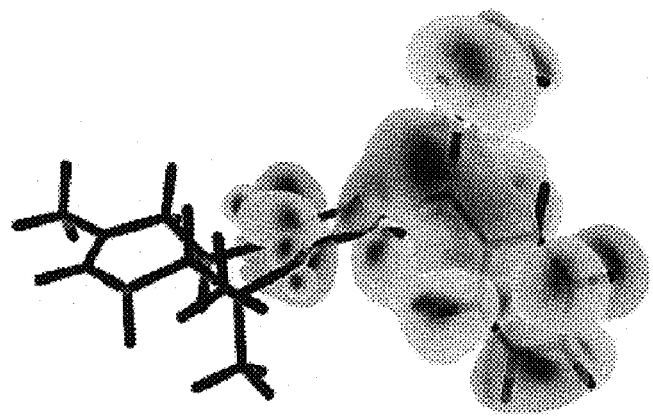
FIG. 15 illustrates a LUMO orbital diagram for the lowest energy conformer of compound 34 (C) as defined in Table 4.
Figure 16:
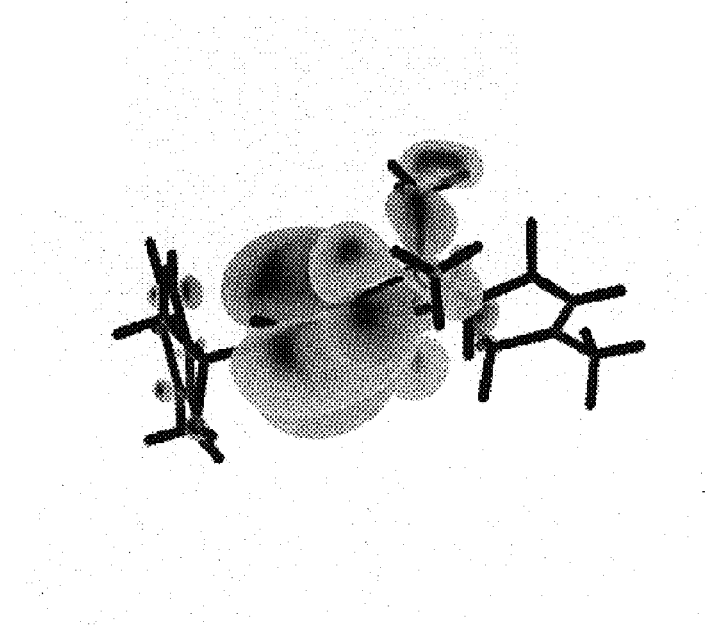
FIG. 16 illustrates a HOMO orbital diagram for the lowest energy conformer of compound 33 (H) as defined in Table 4.
Figure 17:
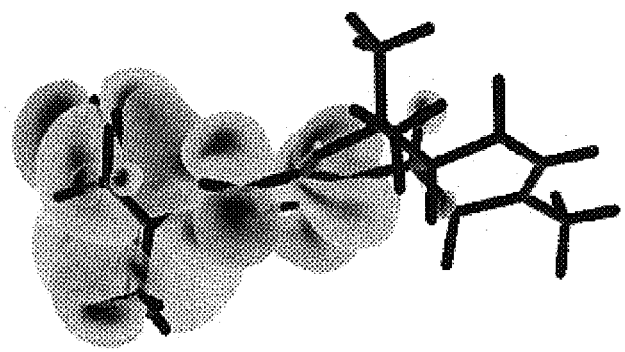
FIG. 17 illustrates a LUMO orbital diagram for the lowest energy conformer of compound 33 (H) as defined in Table 4.
Figure 18:
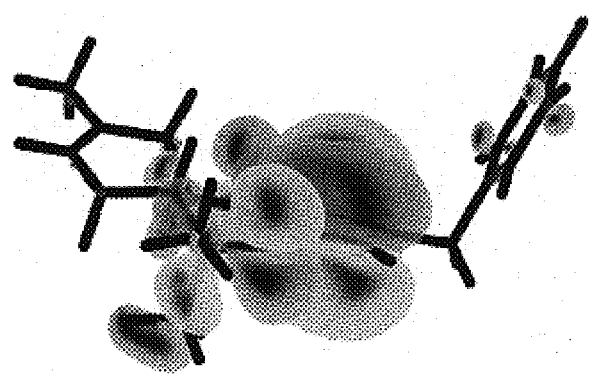
FIG. 18 illustrates a HOMO orbital diagram for the lowest energy conformer of compound 35 (H) as defined in Table 4.
Figure 19:
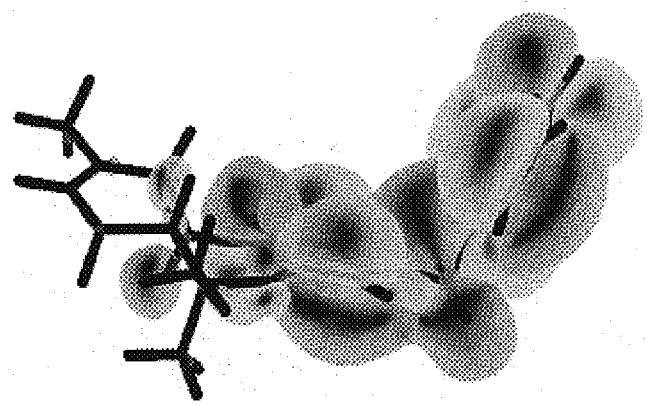
FIG. 19 illustrates a LUMO orbital diagram for the lowest energy conformer of compound 35 (H) as defined in Table 4.
Figure 20:
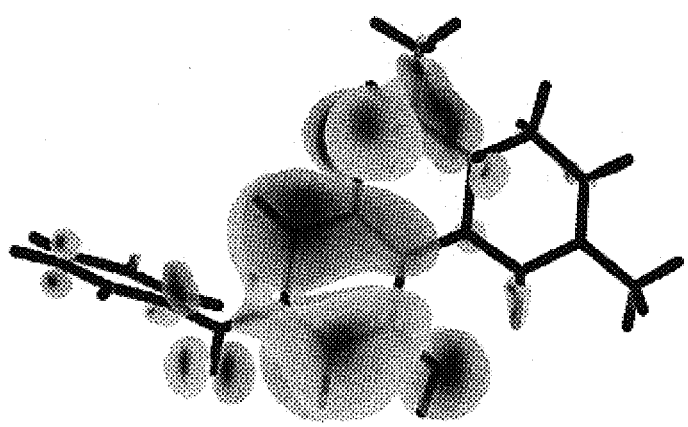
FIG. 20 illustrates a HOMO orbital diagram for the lowest energy conformer of compound 36 (M) as defined in Table 4.
Figure 21:
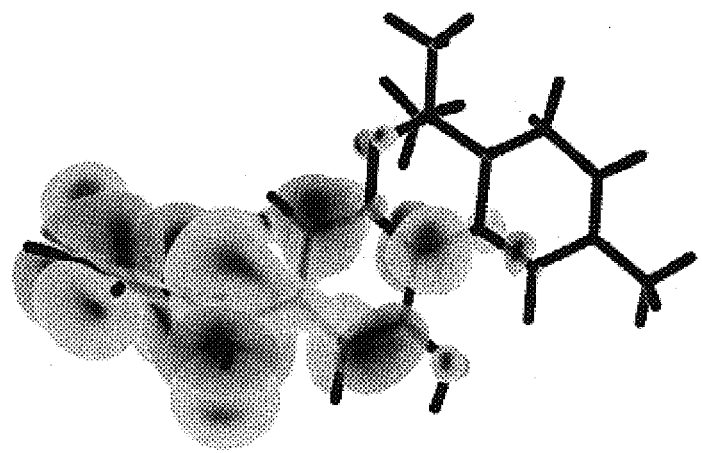
FIG. 21 illustrates a LUMO orbital diagram for the lowest energy conformer of compound 36 (M) as defined in Table 4.

An interesting feature of the potential energy surface emerges from examination of FIGS. 10–13. Aside from the large barriers to rotation for compound 34 and compound 36, there is very little energy associated with rotation about $\tau_1$ for compound 36 and only slightly more for compound 34. This implies that within a particular well on the potential energy surface, these two molecules have a great deal of conformational freedom. In the case of compound 36 this can be explained by considering the $\pi$ conjugation between the carbonyl group and Ring A. The strength of the conjugation creates large barriers to rotation as the necessary orbital overlap is broken leaving the frontside of the molecule free to rotate about the C3—C1' bond until the overlap is reestablished. In the case of compound 34 there is no conjugation to account for this interaction. In fact, the rationale behind the synthesis of the dithiolane derivative was to provide steric bulk sufficient to hinder the rotation of the front-side moiety. The rotational freedom within a potential well can be explained by the influence of the sulfur atoms on the electronic structure of the cannabinoid. If we view the HOMO for the dithiolane derivative (FIG. 14) we see that the electron density associated with this orbital is centered on Ring A of the cannabinoid backbone. However, the LUMO for this molecule (FIG. 15) shifts the electron density to include the substituted phenyl ring and the sulfur atoms in the dithiolane linkage. The sulfur atoms act like an "electron bridge" between the phenyl rings allowing much larger oscillations within the potential well.

Although this yields some insight into the conformational freedom of these molecules, it still does not provide a satisfactory explanation of the NMR experiments. In order to make a proper interpretation, we need to consider all of the available conformations for each of the molecules. In calculating the Hessian for each local minimum the total Gibbs' free energy at 298.15 K was determined. Using these energies, we can apply a Maxwell-Boltzmann average over the likely structures to obtain an "average structure" for each of these molecules. We have applied this Maxwell-Boltzmann analysis in four ways with the results given in Table below. The first column represents a Maxwell-Boltzmann average that assumes complete conformational freedom on the potential energy surface. For this analysis all structures within 0.59 kcal/mol of the lowest energy conformation on the potential energy surface were considered. The second column represents all structures available from free rotation about $\tau_2$ while confining $\tau_2$ to the limits of the potential energy well in which the lowest energy structure was identified. Similarly, the third column represents freedom about $\tau_1$ while restricting $\tau_2$ in the same manner. The last column represents an average of all the local minima identified within a particular potential energy well assuming that the molecule cannot explore any of the other wells on the potential energy surface.

TABLE 7

Structural parameters for the averaged side chain geometries.

| Compound | Energy | | $\tau_1$ restricted | | $\tau_2$ restricted | | Well Confined | |
| --- | --- | --- | --- | --- | --- | --- | --- | --- |
| | $\tau_1$ | $\tau_2$ | $\tau_1$ | $\tau_2$ | $\tau_1$ | $\tau_2$ | $\tau_1$ | $\tau_2$ |
| 34 | 352.8 | 328.1 | 153.6 | 210.7 | 167.5 | 160.7 | 153.7 | 213.3 |
| 33 | 354.0 | 320.1 | 252.2 | 123.4 | 216.9 | 210.9 | 258.4 | 198.5 |
| 35 | 194.3 | 164.9 | 149.4 | 100.1 | 245.8 | 202.7 | 154.7 | 200.3 |
| 36 | 3.8 | 181.3 | 250.8 | 185.2 | 187.3 | 263.5 | 245.7 | 266.7 |

Examining Table 6 and Table 7 provides a means to interpret the NMR data. If we consider compound 33 and compound 35, which were theoretically predicted to have complete conformational freedom on the potential energy surface, we see that indeed the average structure predicted by taking only the low-energy structures agrees well with the experimental structures. This is in stark contrast to the predictions based on simply taking the lowest energy structures as shown in Table 6. Similarly, if we examine the results obtain from the Maxwell-Boltzmann averaging for compound 36 within a single potential well we see good agreement with the experimental results. The only discrepancy appears in the treatment of compound 34. Restricting the analysis to a single potential well in this case predicts a $\tau_1$ angle of 153.7 degrees whereas the NMR experiment observes an angle of 325.1 degrees. Because the dithiolane ring closure is a two step processes, it is conceivable that products from each of the available potential energy wells will form and remain conformationally restricted due to the high rotational energy barriers predicted in the calculations. The influence of the sulfur atoms provides a large amount of rotational freedom within the individual wells and creates a distribution of conformers that appears the same in NMR experiments as the case where complete conformational freedom is assumed. Thus, if we take only the lowest energy structures, as with compound 33 and compound 35, we obtain excellent agreement with NMR experiments. Integrating over the entire potential energy surface using the Maxwell-Boltzmann partition function may provide more insight into the deviations of predicted values for $\tau_1$ and $\tau_2$ from experiment, however this would require calculating the Hessian and the thermodynamic energies at every point.

One of the most interesting features of these cannabinoid derivatives is their electronic structure. We note that the addition of a phenyl ring to the side chain introduces several new orbitals with energies between the original HOMO and LUMO energies of the cyclohexyl derivatives (see FIG. 7). Comparing compound 34 with gem-dimethyl-cyclohexyl-$\Delta^8$-THC and compound 33 with dithiolanyl-cyclohexyl-$\Delta^8$-THC, we see that the orbital energies of the frontier orbitals have been "compressed", providing smaller HOMO-LUMO gaps and adding extra states within the same energy region. We see that there is similar orbital structure in compound 35 and compound 36 and note that the extra π conjugation in compound 36 lowers the LUMO energy to the point of making it a binding orbital. This result is even more interesting when the tendency of DFT to overestimate the energies of unoccupied orbitals is considered.

The HOMO and LUMO orbital diagrams at the B3LYP/6-31G(pd) level of theory for the lowest energy structures of each cannabinoid are shown in FIG. 14–21. For each of the phenyl derivatives in the present study we see that the LUMO provides a non-classical π system with direct overlap between the electron densities on Ring A and the frontside phenyl ring. In the case of compound 34 and compound 36, where the LUMO energies are binding, this provides a mechanism for electron transfer between the two ring structures. Given the low energies for the LUMOs in compound 33 and compound 35 (<0.2 eV each) the same mechanism is likely available to these molecules as well. The presence of such π systems suggests that there may be a mechanism for molecular fluorescence through electron transfer in the absence of the typical n to π* transition. Further investigations regarding the fluorescence of these novel compounds are planned and will be reported elsewhere.

Conclusions

We believe that the structures observed in the NMR experiments represent the time-average of structures in solution. Because of the shallow nature of the wells on the PES there is reason to believe that "rocking" modes about $\tau_1$ and $\tau_2$ are responsible for the experimental observations. This is a significant observation as it represents, to the best of our knowledge, the first theoretical justification for observed NMR structures in this class of compounds. Additionally, we have shown that traditional approaches, which focus primarily on the lowest energy structures of the PES, are insufficient to properly interpret NMR experimental observations.

We believe that this new understanding of the electronic structure of the novel phenyl substituted classical cannabinoids has implications beyond this class of cannabinoids. This is most evident when considering the structurally distinct pyrazole and alkyl amino indole cannabinoid ligands and the efforts of researchers to delineate the unique LBP subsite interactions from the sites shared by all ligands. A consensus has yet to emerge on the LBP interactions with ligands, which may be due, in part, to limited studies directed at studying the electronic properties of all the classes of cannabinoid ligands. We believe that our approach may in fact identify as yet undetermined similarities not readily assessed by molecular mechanics methods. Electronic effects clearly play a role in the geometries of these novel cannabinoids and the understanding of these will likely lead to new approaches in ligand design and methods for ligand synthesis. However there has been no attempt as yet to develop QSAR models based on these calculations. We believe that the future development of E-QSAR (electronic quantitative structure-activity relationships) models will play an important role in understanding the pharmaceutical action of these and other drugs in the future.

Example 7

Synthesis of Substituted 1'-phenyl $\Delta^8$-THC Analogs and 1'-thiophen-2-yl $\Delta^8$-THC Analog Compounds were synthesized substantially as described in Example 5, except that either a substituted-phenyl magnesium bromide or thiophenyl magnesium bromide was used to obtain the corresponding alcohol. Oxidation of alcohol with PCC yielded the key intermediate ketone (Frenette et al., *J. Org. Chem.* 56:3083 (1991), which is hereby incorporated by reference in its entirety). The ketone intermediate was reacted with dimethyl zinc and titanium tetrachloride to form the dimethyl substituent at the C1' position (Singer et al., *J. Med. Chem.* 41:4400 (1998), which is hereby incorporated by reference in its entirety). 1'-substituted gem-dimethyl $\Delta^8$-THC analogs containing a p-methylphenyl (compound 50), m-methylphenyl (compound 51), p-fluorophenyl (compound 52), p-chlorophenyl (compound 53), m-chlorophenyl (compound 54), and thiophenyl (compound 55) were then obtained from the corresponding resorcinols by reacting them with cis-$\Delta^2$-p-menthene-1,8-diol (Prasad et al., *Tetrahedron* 32:1437 (1976), which is hereby incorporated by reference in its entirety) in presence of p-toluene sulfonic acid.

Compound 50: gem-dimethyl-p-methylphenyl-$\Delta^8$-THC or 6,6,9-Trimethyl-3-(1-methyl-1-p-tolyl-ethyl)-6a,7,10,10a-tetrahydro-6H-benzo[c]chromen-1-ol Yield: 0.5449 g (55.6%) as white foam. $R_f$=0.33 (methylene chloride-hexane, 1:1). $^1$H NMR (500 MHz, CDCl$_3$): δ (Ppm) 1.11 (s, 3H), 1.37 (s, 3H), 1.59 (m, 6H), 1.69 (s, 3H), 1.81 (m, 3H), 2.14 (m, 1H), 2.31 (s, 3H), 2.67 (m, 1H), 3.16 (m, 1H), 4.53 (s, 1H), 5.42 (d, J=4.5 Hz, 1H), 5.98 (d, J=2 Hz, 1H), 6.43 (d, J=2 Hz, 1H), 7.07 (d, J=8 Hz, 2H), 7.143 (d, J=8 Hz, 2H); MS: (ESI, Neg) m/z 375.4 [(M−1)$^-$].

Compound 51: gem-dimethyl-m-methylphenyl-$\Delta^8$-THC or 6,6,9-Trimethyl-3-(1-methyl-1-m-tolyl-ethyl)-6a,7,10,10a-tetrahydro-6H-benzo[c]chromen-1-ol Yield: 0.139 g (28.8%) as yellow oil. $R_f$=0.34 (methylene chloride-hexane, 1:1). $^1$H NMR (500 MHz, CDCl$_3$): δ (ppm) 1.12 (s, 3H), 1.38 (s, 3H), 1.59 (m, 6H), 1.69 (s, 3H), 1.82 (m, 3H), 2.14 (m, 1H), 2.31 (s, 3H), 2.68 (m, 1H), 3.17 (m, 1H), 4.52 (s, 1H), 5.42 (d, J=4.5 Hz, 1H), 5.97 (d, J=2 Hz, 1H), 6.43 (d, J=2 Hz, 1H), 6.98 (m, 1H), 7.05 (m, 2H), 7.15 (m, 1H); MS: (ESI, Neg) m/z 375.5 [(M−1)$^-$].

Compound 52: gem-dimethyl-p-chlorophenyl-$\Delta^8$-THC or 3-[1-(4-Chloro-phenyl)-1-methyl-ethyl]-6,6,9-trimethyl-6a,7,10,10a-tetrahydro-6H-benzo[c]chromen-1-ol Yield: 0.6334 g (50.4%) as white foam. $R_f$=0.41 (methylene chloride-hexane, 1:1). $^1$H NMR (500 MHz, CDCl$_3$): δ (ppm) 1.04 (s, 3H), 1.30 (s, 3H), 1.51 (m, 6H), 1.62 (s, 3H), 1.75 (m, 3H), 2.07 (m, 1H), 2.61 (m, 1H), 3.09 (m, 1H), 4.49 (s, 1H), 5.35 (d, J=5 Hz, 1H), 5.89 (d, J=2 Hz, 1H), 6.30 (d, J=2 Hz, 1H), 7.09 (d, J=8.5 Hz, 2H), 7.15 (d, J=9 Hz, 2H); MS: (ESI, Neg) m/z 395.9 [(M−1)$^-$].

Compound 53: gem-dimethyl-m-chlorophenyl-Δ$^8$-THC or 3-[1-(3-Chloro-phenyl)-1-methyl-ethyl]-6,6,9-trimethyl-6a,7,10,10a-tetrahydro-6H-benzo[c]chromen-1-ol Yield: 0.6597 g (50.6%) as a white solid. $R_f$=0.37 (methylene chloride-hexane, 1:1). $^1$H NMR (500 MHz, CDCl$_3$): δ (ppm) 1.04 (s, 3H), 1.30 (s, 3H), 1.51 (m, 6H), 1.62 (s, 3H), 1.75 (m, 3H), 2.07 (m, 1H), 2.61 (m, 1H), 3.09 (m, 1H), 4.51 (s, 1H), 5.35 (d, J=4.5 Hz, 1H), 5.89 (d, J=1.5 Hz, 1H), 6.31 (d, J=1.5 Hz, 1H), 7.07 (m, 3H), 7.17 (m, 1H); MS: (ESI, Neg) m/z 395.9 [(M−1)$^-$].

Compound 54: gem-dimethyl-p-fluorophenyl-Δ$^8$-THC or 3-[1-(4-Fluoro-phenyl)-1-methyl-ethyl]-6,6,9-trimethyl-6a,7,10,10a-tetrahydro-6H-benzo[c]chromen-1-ol Yield: 0.5919 g (45.5%) as light pink foam. $R_f$=0.37 (methylene chloride-hexane, 1:1). $^1$H NMR (500 MHz, CDCl$_3$): δ (ppm) 1.04 (s, 3H), 1.30 (s, 3H), 1.51 (m, 6H), 1.62 (s, 3H), 1.75 (m, 3H), 2.07 (m, 1H), 2.61 (m, 1H), 3.09 (m, 1H), 4.49 (s, 1H), 5.35 (d, J=4.5 Hz, 1H), 5.90 (d, J=2 Hz, 1H), 6.32 (d, J=2 Hz, 1H), 6.86 (m, 2H), 7.12 (m, 2H); MS: (ESI, Neg) m/z 379.5 [(M−1)$^-$].

Compound 55: gem-dimethyl-thiophenyl-Δ$^8$-THC or 6,6,9-Trimethyl-3-(1-methyl-1-thiophen-2-yl-ethyl)-6a,7,10,10a-tetrahydro-6H-benzo[c]chromen-1-ol Yield: 0.1176 g (21.9%) as white foam. $R_f$=0.37 (methylene chloride-hexane, 1:1). $^1$H NMR (500 MHz, CDCl$_3$): δ (ppm) 1.04 (s, 3H), 1.30 (s, 3H), 1.63 (m, 9H), 1.74 (m, 3H), 2.07 (m, 1H), 2.61 (m, 1H), 3.10 (m, 1H), 4.50 (s, 1H), 5.35 (d, J=4.5 Hz, 1H), 6.04 (d, J=2 Hz, 1H), 6.38 (d, J=2 Hz, 1H), 6.76 (dd, J=1.5 Hz, 3.5 Hz, 1H), 6.84 (m, 1H), 7.07 (dd, J=1 Hz, 5 Hz, 1H); MS: (ESI, Neg) m/z 367.4 [(M−1)$^-$].

Example 8

Receptor Binding Assays

Receptor binding assays were performed on compounds 50–55 as described in the Materials and Methods (for Examples 1–4) and in Example 2 to determine their binding affinities on the CB-1 and CB-2 receptors (see Table 8 below).

The $K_i$ values for Δ$^8$-THC at the hCB1 and hCB2 receptor were 28.5 nM and 25.0 nM, respectively (affinity ratio CB1/CB2=1.14), compared to a reported value of 47.6 nM for the rCB1 and 39.3 for the mCB2 (affinity ratio CB1/CB2=1.21)(Busch-Ptersen, J. et al., *J. Med. Chem.* 39:3790 (1996), which is hereby incorporated by reference in its entirety). Relative to Δ$^8$-THC, all of the compounds showed enhanced affinity to both the CB-1 and the CB-2 receptors, except for the gem-dimethyl-p-fluorophenyl Δ$^8$-THC analog (which did show enhanced affinity for the CB-2 receptor). Otherwise, these analogs exhibited up to a 93 fold enhancement in binding affinity to the receptor subtypes relative to Δ$^8$-THC. Of particular note is that both the gem-dimethyl-p-methylphenyl and gem-dimethyl-2-thiophene analogs possessed sub-nanomolar affinities for the CB-2 receptor, with some degree of selectivity for the CB-2 receptor. Both of these compounds showed improved affinity for CB-1 and CB-2 receptors relative to the gem-dimethyl-phenyl Δ$^8$-THC analog. Also of note is that the gem-dimethyl-p-chlorophenyl analog exhibited improved selectivity for the CB-2 receptor.

TABLE 8

Binding affinities of $^8$Δ-THC and substituted phenyl analogs 50–55 for the CB1 and CB2 receptors

| Compound | CB$_1$ K$_i$ (nM)[a] | CB$_2$ K$_i$ (nM)[a] | Ratio CB$_1$/CB$_2$ |
|---|---|---|---|
| $^8$Δ-THC | 28.5 (±3.3) | 25.0 (±4.8) | 1.14 |
| 50 | 2.13 (±0.37) | 0.88 (0.05) | 3.56 |
| 51 | 2.53 (±0.54) | 1.13 (±0.02) | 2.24 |
| 52 | 76.1 (±15.5) | 12.4 (±0.24) | 6.14 |
| 53 | 18.8 (±1.39) | 1.68 (±0.2) | 11.2 |
| 54 | 2.80 (±0.05) | 3.54 (±0.71) | 0.79 |
| 55 | 1.08 (±0.04) | 0.27 (±0.01) | 4.00 |
| 33 | 12.3 (±0.61) | 0.91 (±0.08) | 13.5 |

[a]The K$_i$ values for $^8$Δ-THC and the analogs were obtained from n ≧ 2 independent experiments run in triplicate showing the standard error of the mean in parentheses.

Example 9

Use of gem-dimethyl-cyclohexyl Δ$^8$-THC Analog for Treatment of Hemorrhagic Shock The rat hemorrhagic shock model as modified by Wagner et al. (*Nature* 390: 518–521 (1997), which is hereby incorporated by reference in its entirety) was used to test drug combinations that exhibit selective constriction vasoactivity. Male Sprague-Dawley rats, 300–350 g, 4 months of age, were first anesthetized using isoflo and then anesthetized by injection of urethane (0.7 g/kg i.p. followed by 0.3 g/kg i.v.). Body temperature was maintained at ~37° C. by convective heating. The animals were restrained in the supine position by tying the hind legs to the mounting board. The groin area was be shaved on the left limb, which was incised to expose the femoral neurovascular bundle. The left femoral vein and artery were canulated with P50 tubing and tied firmly into place using 4-0 silk thread. A midline incision was made in the ventro-cervical region and the underlying tissues bisected laterally to expose the carotid artery. Into the artery was inserted the 1.4F (0.56 mm) Millar catheter pressure transducer for monitoring blood pressure and heart rate. It was firmly tied into place using 4-0 silk thread. The left femoral vein was used for drug injections and the left femoral artery used for bleeding and sampling. The animal underwent a step-wise bleeding following the surgical procedures until the mean blood pressure stabilizes at 40 mm Hg. Initial drug injections were administered based on the mg/kg dosing determined in the intravital microscopy studies 5 min after the induction of shock or just prior to shock induction. The endpoint of these studies was the expiration of the animal or euthanasia when the animal is in severe distress. Survival time, blood pressure, and heart rate were recorded and compared to control animals that received only vehicle. A minimum of six animals were used per study from which the mean survival time was determined. Successful drug combinations are defined as those that at least double the survival time of the animals relative to controls that receive either vehicle or a single drug. Sucessful responses are monitored for a maximum of four hours.

Figure 22:
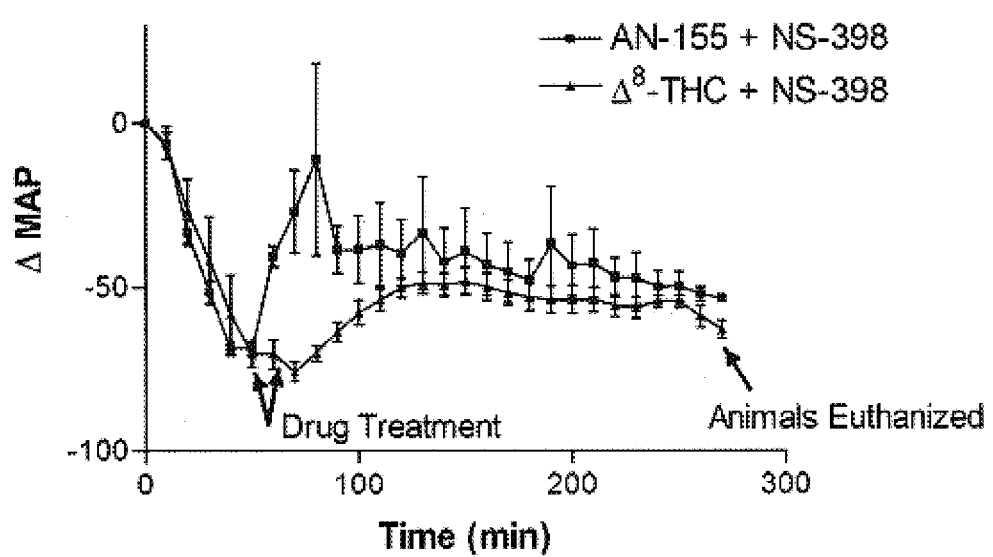
FIG. 22 is a graph illustrating the change in mean blood pressure versus time for administration of compound 25 or $\Delta^8$-THC (12 mg/kg) in combination with NS-398 (2 mg/kg) during a hemorrhagic shock protocol. Compound 25 demonstrated improved behavior relative to the positive control of $\Delta^8$-THC and NS-398. As used in the legend of FIG. 22, AN-155 refers to compound 25 and NS-398 refers to a COX-2 inhibitor.
Figure 23:
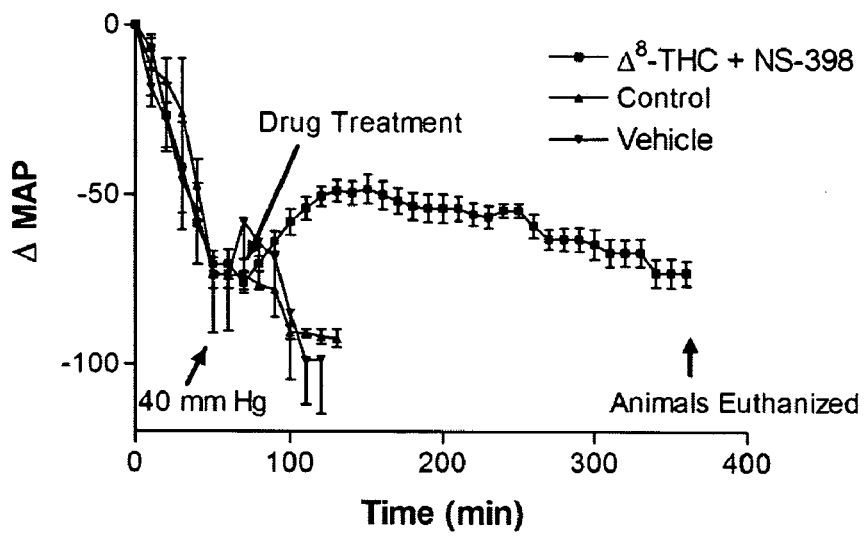
FIG. 23 is a graph illustrating the change in mean blood pressure versus time for administration of negative controls relative to the positive control of $\Delta^8$-THC and NS-398 during the hemorrhagic shock protocol.

Experiments using gem-dimethyl-cyclohexyl Δ$^8$-THC were carried out using 12 mg/kg gem-dimethyl-cyclohexyl Δ$^8$-THC or Δ$^8$-THC and 2 mg/kg NS-398 (a COX-2 inhibitor). The result of these experiments are shown in FIG. 22. A comparison of untreated animals is shown in FIG. 23. The animals subjected to hemorrhagic shock and treated with the binary therapy, i.e., cannabinoid receptor 1 agonist/COX-2 inhibitor, exhibited a significant increase in survival time relative to control animals. However, animals treated with the high affinity CB1 ligand gem-dimethyl-cyclohexyl Δ⁸-THC exhibited a rapid increase in ΔMAP that reached within 85 percent of basal MAP levels followed by a decline in ΔMAP that paralleled the response to Δ⁸-THC. The overall profiles suggest that the novel cannabinoid analogs provide greater efficacy in the hemorrhagic shock binary therapy.

Example 10

Figure 24:
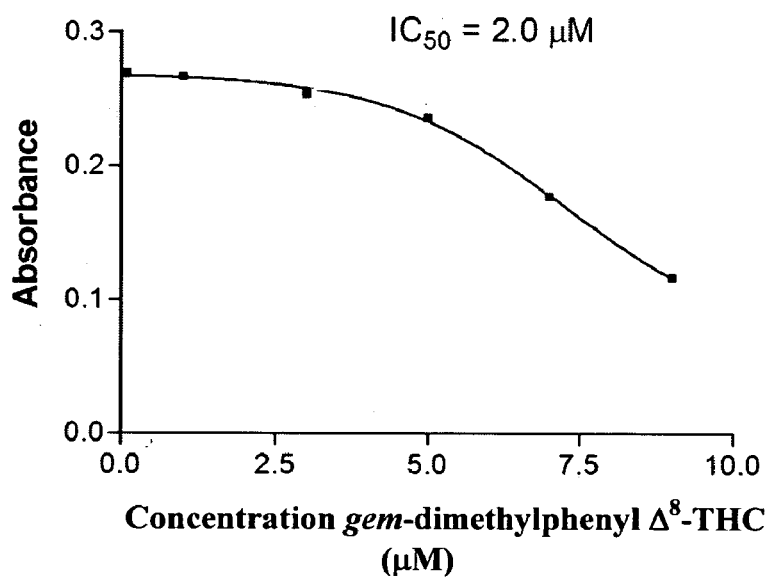
FIG. 24 is a graph illustrating the IC$_{50}$ for cytotoxic effect of gem-dimethyl-phenyl $\Delta^8$-THC (compound 33) on C6 glioma cells.

In vitro Determination of $IC_{50}$ for gem-dimethyl-phenyl Δ⁸-THC Analog on C6 Glioma Cells To determine the $IC_{50}$ for gem-dimethyl-phenyl Δ⁸-THC analog with respect to cytotoxicity, a dose escalation study was done measuring the cytotoxic effects of the compound against C6 glioma. C6 glioma cells were plated in triplicate in 96-well flat-bottom plates at 70% confluency in a 100 μl total volume of supplemented Hams/F12 medium and incubated overnight at 37° C. to allow for adherence. The cultures were then treated with escalating concentrations of the compound ranging from 0.1 to 9 uM. All drug stimulation was done in the appropriate supplemented media formulated with 0.5% DMSO, but serum was restricted to 1% to prevent binding of drug by components of serum. Following the addition of drugs, cell death was analyzed at 48 h using the CellTiter 96R Non-Radioactive Cell Proliferation assay (G5421, Promega, Madison, Wis.). The percentage of viable cells present in the culture at each time point was calculated by comparing the absorbance value at 492 mn from the MTS reaction using a Lab Systems Multiskan Biochromatic Elisa plate reader (Vienna, Va.). All described values represent the average of three data points, the results of these assays are shown in FIG. 24.

Glioblastoma multiforme (GBM) is the most common and malignant of all the primary brain tumors with a median survival for most patients with high-grade glioma being on order of months. While may anti-neoplastic agents have good in vitro activity however, the difficulty in delivery to the CNS limits their use. The $IC_{50}$ observed for gem-dimethyl-phenyl Δ⁸-THC, the fact that complete cell death occurs within 5 hours at concentrations of 8 μM, and the well established CNS permeability of cannabinoids supports the use of the novel cannabinoids as anti-glioma agents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound according to formula (I)

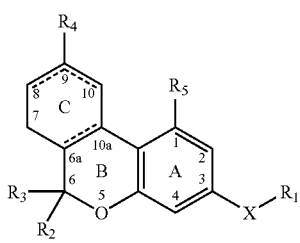

(I)

wherein,

X is selected from the group of $C(CH_3)_2$, $C(—Y(CH_2)_n Y—)$, $CH_2$, $C(O)$,

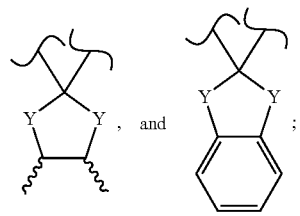

, and ;

Y is selected from the group of S and O;
$R_1$ is selected from the group of a C3 to C8 cycloalkyl, biphenyl,

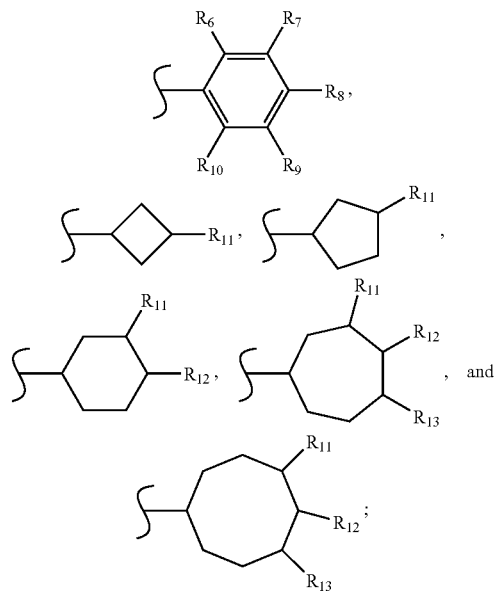

with the proviso that, when X is $CH_2$, $R_1$ is not cycloexyl or phenyl;
$R_2$ and $R_3$ are methyl;
$R_4$ is selected from the group of methyl, methanol, —$(CH_2)_m COOH$, and —$(CH_2)_m COH$;
$R_5$ is selected from the group of H, OH, methoxy, and ethoxy;
$R_6$–$R_{10}$ are independently selected from the group of H, OH, C1 to C6 alkyl, halo, amino, C1 to C2 alkylamino, C1 to C2 dialkylamino, amido, C1 to C2 alkylamido, cyano, nitro, C1 to C6 alkoxy, C1 to C6 alcohol, carboxyl containing a C1 to C6 alkyl, carbonyl containing a C1 to C6 alkyl, ester containing a C1 to C6 alkyl group, sulfoxide containing a C1 to C6 alkyl, and sulfone containing a C1 to C6 alkyl;
at least one of $R_{11}$–$R_{13}$ is selected from the group of C1 to C6 alkyl, C1 to C6 alkoxy, fluoro, and chloro, and the other of $R_{11}$–$R_{13}$ can optionally be H;
n is an integer from 2 to 4; and
m is an integer that is either 0 or 1.

2. The compound according to claim 1 wherein $R_2$, $R_3$, and $R_4$ are methyl; and
$R_5$ is OH.

3. The compound according to claim 2 wherein X is $C(CH_3)_2$.

4. The compound according to claim 3 wherein $R_1$ is a C5 to C7 cycloalkyl,

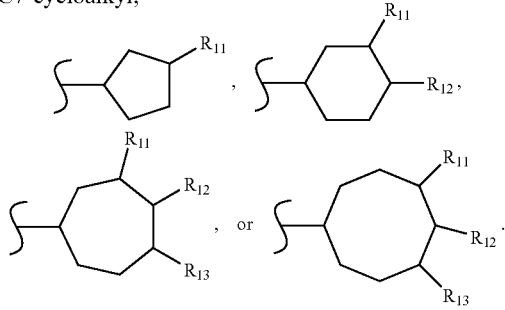

5. The compound according to claim 3 wherein $R_1$ is phenyl, p-methylphenyl, or m-methylphenyl.

6. The compound according to claim 2 wherein X is $C(-Y(CH_2)_nY-)$.

7. The compound according to claim 2 wherein X is $CH_2$.

8. The compound according to claim 2 wherein X is $C(O)$.

9. The compound according to claim 8 wherein $R_1$ is a C5 to C7 cycloalkyl,

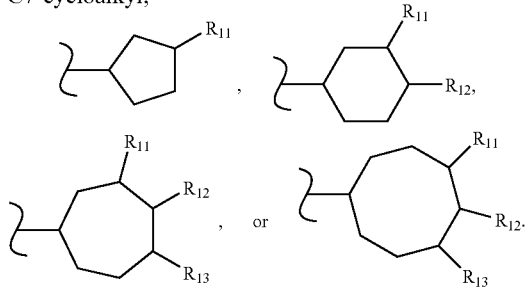

10. The compound according to claim 2 wherein $R_1$ is a C3 to C8 cycloalkyl,

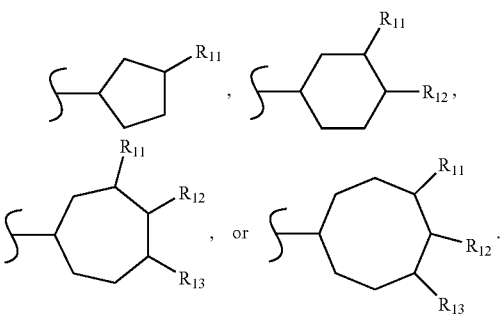

11. The compound according to claim 2 wherein $R_1$ is phenyl, o-methylphenyl, m-methylphenyl, p-methylphenyl, m,p-dimethylphenyl, o,p-dimethylphenyl, m-ethylphenyl, p-ethylphenyl, m,p-diethylphenyl, p-chlorophenyl, p-fluorophenyl, p-bromophenyl, m-aminophenyl, p-aminophenyl, m-methylaminophenyl, p-methylaminophenyl, N,N-dimethyl-m-aminophenyl, N,N-dimethyl-p-aminophenyl, m-cyanophenyl, p-cyanophenyl, m-nitrophenyl, p-nitrophenyl, o-methoxyphenyl, m-methoxyphenyl, p-methoxyphenyl, m-ethoxyphenyl, p-ethoxyphenyl, m-hydroxyphenyl, p-hydroxyphenyl, m-methylsulfone-phenyl, p-methylsulfone-phenyl, m-ethylsulfone-phenyl, p-ethylsulfone-phenyl, m-methylsulfoxide-phenyl, p-methylsulfoxide-phenyl, m-ethylsulfoxide-phenyl, or p-ethylsulfoxide-phenyl.

12. The compound according to claim 1 wherein ring C contains a Δ8 double bond.

13. The compound according to claim 1 wherein ring C contains a Δ9 double bond.

* * * * *